(12) United States Patent
Harberd et al.

(10) Patent No.: US 6,830,930 B2
(45) Date of Patent: Dec. 14, 2004

(54) **NUCLEIC ACID ENCODING GAI GENE OF *ARABIDOPSIS THALIANA***

(75) Inventors: Nicholas P. Harberd, Norwich (GB); Jinrong Peng, Norwich (GB); Pierre Carol, Grenoble Cédex (FR); Donald E. Richards, Norwich (GB)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 09/911,513

(22) Filed: Jul. 25, 2001

(65) Prior Publication Data

US 2002/0049995 A1 Apr. 25, 2002

Related U.S. Application Data

(63) Continuation of application No. 09/117,853, filed as application No. PCT/GB97/00390 on Feb. 12, 1997, now Pat. No. 6,307,126.

(30) Foreign Application Priority Data

Feb. 12, 1996 (GB) ............................................. 9602796

(51) Int. Cl.$^7$ ........................ C12N 15/29; C12N 15/82; C12N 15/90; A01H 1/00; A01H 5/00
(52) U.S. Cl. .................... 435/468; 435/320.1; 435/419; 536/23.6; 800/260; 800/290
(58) Field of Search ............................. 435/69.1, 320.1, 435/410, 419, 468, 471; 536/23.6; 800/278, 260, 290, 295, 298

(56) References Cited

U.S. PATENT DOCUMENTS 6,307,126 B1 * 10/2001 Harberd et al. ............. 800/290

FOREIGN PATENT DOCUMENTS

WO   WO 95 02060   1/1995   ........... C12N/15/82

OTHER PUBLICATIONS

Plant Cell, vol. 5, Mar. 1993, MD US, pp. 351–360, Peng et al, "Derivative alleles of the *Arabidopsis* Gibberellin–insensitive (gai) mutation confer a wild type phenotype".
Plant Physiology, vol. 106, Dec. 1994, MD US, pp. 1241–1255, Newman et al, "Genes Galore: a summary of methods for accessing results from large–scale partial sequencing of anonymous *Arabidopsis* cDNA clones".

EMBL Database, Heidelberg, DE, Acc. Nr. Z34183, Jun. 6, 1994, Desprez et al, "The *Arabidopsis thaliana* transcribed genome: the GDR cDNA program".
Plant Physiology, vol. 108, Jun. 1995, MD US, pp. 495–502, Wilson et al, "Phenotypic suppression of the gibberellin–insensitive mutant (gai) of Aradipsis".
Plant Molecular Biology, vol. 26, Dec. 1994, Dordrecht NL, pp. 1529–1555, Hooley, "Gibberellins: perception, transduction and responses".
Genetics, vol. 121, Apr. 1989, pp. 827–838, Harberd et al, "genetics of dominant gibberellin–insensitive dwarfism in maize".
Planta, vol. 197, No. 2, Sep. 1995, pp. 414–417, Carol et al, "Isolation and preliminary characterization of gas 1–1, a mutation causing partial suppression of the phenotype conferred by the gibberellin–insensitive (gai) mutation in *Arabidopsis thaliana* (L.) Heyhn".
Truong et al, "Sequence and characterization of two *Arabidopsis thaliana* cDNAs isolated by functional complementation of a yeast *gln3 gdh1* mutant", FEBS Letters 410:213–218 (1997).
Peng et al, "The *Arabodopsis* GAI gene defines a signaling pathway that negatively regulate gibberellin responses", Genes & Development 11:3194–3205 (1997).
Peng et al, "'Green revolution' genes encode mutant gibberellin response modulators", Nature 400:256–261 (1999).
Xu et al, "Evaluation of the Arabidopsis GAI/gai Gene(s) in Transgenic Maize", Abstract—from a poster presented to the 10th International Plant Tissue Culture and Biotechnology Congress in 2002.
Fu et al, "Expression of *Arabidopsis* GAI in Transgenic Rice Represses Multiple Gibberellin Response", The Plant Cell 13:1791–1802 (2001).

* cited by examiner

*Primary Examiner*—Ashwin Mehta
(74) *Attorney, Agent, or Firm*—Nixon & Vanderhye PC

(57) ABSTRACT

The GAI gene of *Arabidopsis thaliana* has been cloned, along with mutant and homologue gene sequences. Expression of such genes a plants affects characteristics in the plants including growth. GAI expression inhibits growth of plants, which inhibition is antagonized by gibberellin (GA). Expression of gai mutants confers a dwarf phenotype which is GA-insensitive. Manipulation of expression of GAI and gai genes in plants results in tall or dwarfed plants. Dwarf plants are useful in particular for reduction in crop losses resulting from lodging.

17 Claims, 13 Drawing Sheets

Figure 3

```
TAATAATCAT TTTTTTTCTT ATAACCTTCC TCTCTATTTT TACAATTTAT TTTGTTATTA    60
GAAGTGGTAG TGGAGTGAAA AAACAAATCC TAAGCAGTCC TAACCGATCC CCGAAGCTAA   120
AGATTCTTCA CCTTCCCAAA TAAAGCAAAA CCTAGATCCG ACATTGAAGG AAAAACCTTT   180
TAGATCCATC TCTGAAAAAA AACCAACCAT GAAGAGAGAT CATCATCATC ATCATCAAGA   240
TAAGAAGACT ATGATGATGA ATGAAGAAGA CGACGGTAAC GGCATGGATG AGCTTCTAGC   300
TGTTCTTGGT TACAAGGTTA GGTCATCGGA AATGGCTGAT GTTGCTCAGA AACTCGAGCA   360
GCTTGAAGTT ATGATGTCTA ATGTTCAAGA AGACGATCTT TCTCAACTCG CTACTGAGAC   420
TGTTCACTAT AATCCGGCGG AGCTTTACAC GTGGCTTGAT TCTATGCTCA CCGACCTTAA   480
TCCTCCGTCG TCTAACGCCG AGTACGATCT TAAAGCTATT CCCGGTGACG CGATTCTCAA   540
TCAGTTCGCT ATCGATTCGG CTTCTTCGTC TAACCAAGGC GGCGGAGGAG ATACGTATAC   600
TACAAACAAG CGGTTGAAAT GCTCAAACGG CGTCGTGGAA ACCACCACAG CGACGGCTGA   660
GTCAACTCGG CATGTTGTCC TGGTTGACTC GCAGGAGAAC GGTGTGCGTC TCGTTCACGC   720
GCTTTTGGCT TGCGCTGAAG CTGTTCAGAA GGAGAATCTG ACTGTGGCGG AAGCTCTGGT   780
GAAGCAAATC GGATTCTTAG CTGTTTCTCA AATCGGAGCT ATGAGAAAAG TCGCTACTTA   840
CTTCGCCGAA GCTCTCGCGC GGCGGATTTA CCGTCTCTCT CCGTCGCAGA GTCCAATCGA   900
CCACTCTCTC TCCGATACTC TTCAGATGCA CTTCTACGAG ACTTGTCCTT ATCTCAAGTT   960
CGCTCACTTC ACGGCGAATC AAGCGATTCT CGAAGCTTTT CAAGGGAAGA AAAGAGTTCA  1020
TGTCATTGAT TTCTCTATGA GTCAAGGTCT TCAATGGCCG GCGCTTATGC AGGCTCTTGC  1080
GCTTCGACCT GGTGGTCCTC CTGTTTTCCG GTTAACCGGA ATTGGTCCAC CGGCACCGGA  1140
TAATTTCGAT TATCTTCATG AAGTTGGGTG TAAGCTGGCT CATTTAGCTG AGGCGATTCA  1200
CGTTGAGTTT GAGTACAGAG GATTTGTGGC TAACACTTTA GCTGATCTTG ATGCTTCGAT  1260
GCTTGAGCTT AGACCAAGTG AGATTGAATC TGTTGCGGTT AACTCTGTTT TCGAGCTTCA  1320
CAAGCTCTTG GGACGACCTG GTGCGATCGA TAAGGTTCTT GGTGTGGTGA ATCAGATTAA  1380
ACCGGAGATT TTCACTGTGG TTGAGCAGGA ATCGAACCAT AATAGTCCGA TTTTCTTAGA  1440
TCGGTTTACT GAGTCGTTGC ATTATTACTC GACGTTGTTT GACTCGTTGG AAGGTGTACC  1500
GAGTGGTCAA GACAAGGTCA TGTCGGAGGT TTACTTGGGT AAACAGATCT GCAACGTTGT  1560
GGCTTGTGAT GGACCTGACC GAGTTGAGCG TCATGAAACG TTGAGTCAGT GGAGGAACCG  1620
GTTCGGGTCT GCTGGGTTTG CGGCTGCACA TATTGGTTCG AATGCGTTTA AGCAAGCGAG  1680
TATGCTTTTG GCTCTGTTCA ACGGCGGTGA GGGTTATCGG GTGGAGGAGA GTGACGGCTG  1740
TCTCATGTTG GGTTGGCACA CACGACCGCT CATAGCCACC TCGGCTTGGA AACTCTCCAC  1800
CAATTAGATG GTGGCTCAAT GAATTGATCT GTTGAACCGG TTATGATGAT AGATTTCCGA  1860
CCGAAGCCAA ACTAAATCCT ACTGTTTTTC CCTTTGTCAC TTGTTAAGAT CTTATCTTTC  1920
ATTATATTAG GTAATTGAAA AATTTCTAAA TTACTCACAC TGGC                   1964
```

Figure 4

| | |
|---|---|
| MetLysArgAspHisHisHisHisHisGlnAspLysLysThrMetMetMetAsnGluGlu | 20 |
| AspAspGlyAsnGlyMet<u>AspGluLeuLeuAlaValLeuGlyTyrLysValArgSerSer</u> | 40 |
| <u>GluMetAla</u>AspValAlaGlnLysLeuGluGlnLeuGluValMetMetSerAsnValGln | 60 |
| GluAspAspLeuSerGlnLeuAlaThrGluThrValHisTyrAsnProAlaGluLeuTyr | 80 |
| ThrTrpLeuAspSerMetLeuThrAspLeuAsnProProSerSerAsnAlaGluTyrAsp | 100 |
| LeuLysAlaIleProGlyAspAlaIleLeuAsnGlnPheAlaIleAspSerAlaSerSer | 120 |
| SerAsnGlnGlyGlyGlyGlyAspThrTyrThrThrAsnLysArgLeuLysCysSerAsn | 140 |
| GlyValValGluThrThrThrAlaThrAlaGluSerThrArgHisValValLeuValAsp | 160 |
| SerGlnGluAsnGlyValArgLeuValHisAlaLeuLeuAlaCysAlaGluAlaValGln | 180 |
| LysGluAsnLeuThrValAlaGluAlaLeuValLysGlnIleGlyPheLeuAlaValSer | 200 |
| GlnIleGlyAlaMetArgLysValAlaThrTyrPheAlaGluAlaLeuAlaArgArgIle | 220 |
| TyrArgLeuSerProSerGlnSerProIleAspHisSerLeuSerAspThrLeuGlnMet | 240 |
| HisPheTyrGluThrCysProTyrLeuLysPheAlaHisPheThrAlaAsnGlnAlaIle | 260 |
| LeuGluAlaPheGlnGlyLysLysArgValHisValIleAspPheSerMetSerGlnGly | 280 |
| LeuGlnTrpProAlaLeuMetGlnAlaLeuAlaLeuArgProGlyGlyProProValPhe | 300 |
| ArgLeuThrGlyIleGlyProProAlaProAspAsnPheAspTyrLeuHisGluValGly | 320 |
| CysLysLeuAlaHisLeuAlaGluAlaIleHisValGluPheGluTyrArgGlyPheVal | 340 |
| AlaAsnThrLeuAlaAspLeuAspAlaSerMetLeuGluLeuArgProSerGluIleGlu | 360 |
| SerValAlaValAsnSerValPheGluLeuHisLysLeuLeuGlyArgProGlyAlaIle | 380 |
| AspLysValLeuGlyValValAsnGlnIleLysProGluIlePheThrValValGluGln | 400 |
| GluSerAsnHisAsnSerProIlePheLeuAspArgPheThrGluSerLeuHisTyrTyr | 420 |
| SerThrLeuPheAspSerLeuGluGlyValProSerGlyGlnAspLysValMetSerGlu | 440 |
| ValTyrLeuGlyLysGlnIleCysAsnValValAlaCysAspGlyProAspArgValGlu | 460 |
| ArgHisGluThrLeuSerGlnTrpArgAsnArgPheGlySerAlaGlyPheAlaAlaAla | 480 |
| HisIleGlySerAsnAlaPheLysGlnAlaSerMetLeuLeuAlaLeuPheAsnGlyGly | 500 |
| GluGlyTyrArgValGluGluSerAspGlyCysLeuMetLeuGlyTrpHisThrArgPro | 520 |
| LeuIleAlaThrSerAlaTrpLysLeuSerThrAsn | 532 |

Figure 5
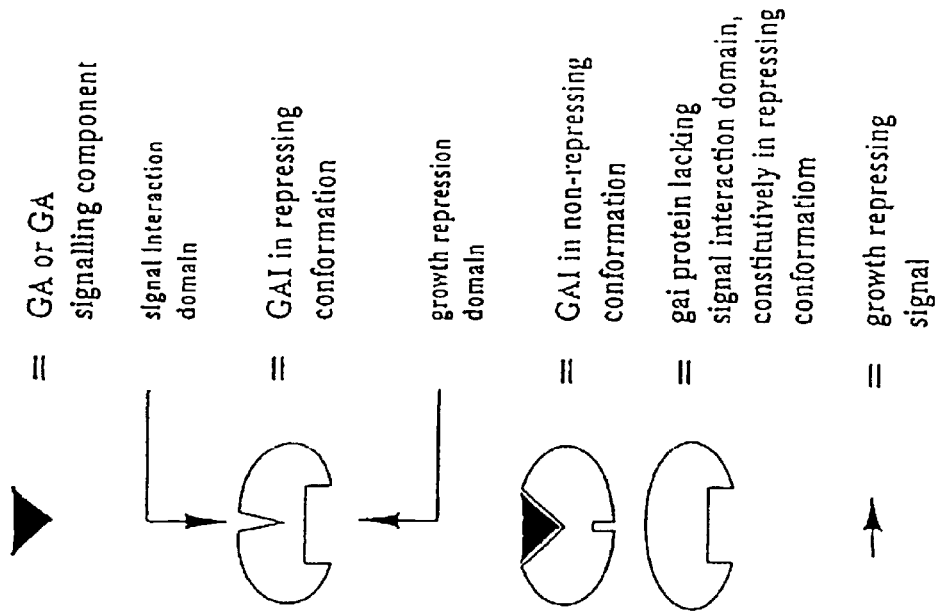
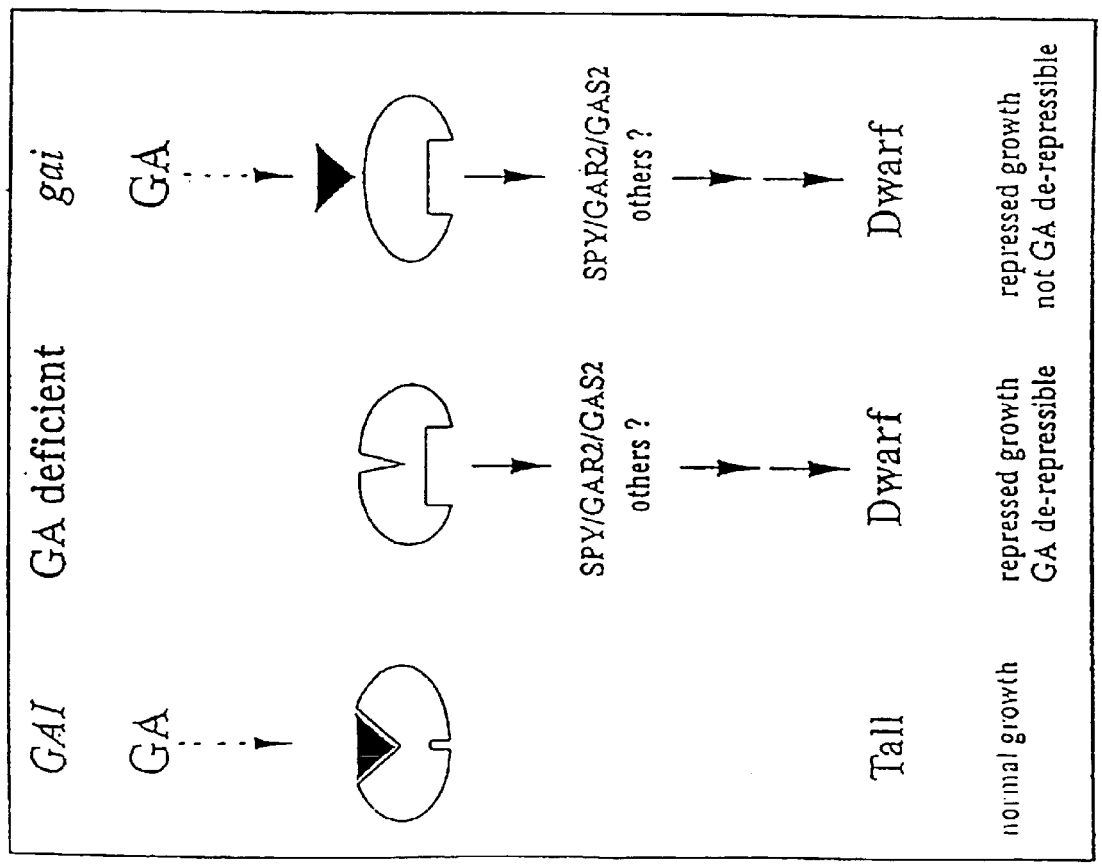

Figure 6(a)

```
   1 TAGAAGTGGT AGTGGAGTGA AAAACAAAT  CCTAAGCAGT CCTAACCGAT
  51 CCCCGAAGCT AAAGATTCTT CACCTTCCCA AATAAAGCAA AACCTAGATC
 101 CGACATTGAA GGAAAAACCT TTTAGATCCA TCTCTGAAAA AAAACCAACC
 151 ATGAAGAGAG ATCATCATCA TCATCATCAA GATAAGAAGA CTATGATGAT
 201 GAATGAAGAA GACGACGGTA ACGGCATGGA TGTTGCTCAG AAACTCGAGC
 251 AGCTTGAAGT TATGATGTCT AATGTTCAAG AAGACGATCT TTCTCAACTC
 301 GCTACTGAGA CTGTTCACTA TAATCCGGCG GAGCTTTACA CGTGGCTTGA
 351 TTCTATGCTC ACCGACCTTA ATCCTCCGTC GTCTAACGCC GAGTACGATC
 401 TTAAAGCTAT TCCCGGTGAC GCGATTCTCA ATCAGTTCGC TATCGATTCG
 451 GCTTCTTCGT CTAACCAAGG CGGCGGAGGA GATACGTATA CTACAAACAA
 501 GCGGTTGAAA TGCTCAAACG GCGTCGTGGA AACCACCACA GCGACGGCTG
 551 AGTCAACTCG GCATGTTGTC CTGGTTGACT CGCAGGAGAA CGGTGTGCGT
 601 CTCGTTCACG CGCTTTTGGC TTGCGCTGAA GCTGTTCAGA AGGAGAATCT
 651 GACTGTGGCG GAAGCTCTGG TGAAGCAAAT CGGATTCTTA GCTGTTTCTC
 701 AAATCGGAGC TATGAGAAAA GTCGCTACTT ACTTCGCCGA AGCTCTCGCG
 751 CGGCGGATTT ACCGTCTCTC TCCGTCGCAG AGTCCAATCG ACCACTCTCT
 801 CTCCGATACT CTTTAGATGC ACTTCTACGA GACTTGTCCT TATCTCAAGT
 851 TCGCTCACTT CACGGCGAAT CAAGCGATTC TCGAAGCTTT TCAAGGGAAG
 901 AAAAGAGTTC ATGTCATTGA TTTCTCTATG AGTCAAGGTC TTCAATGGCC
 951 GGCGCTTATG CAGGCTCTTG CGCTTCGACC TGGTGGTCCT CCTGTTTTCC
1001 GGTTAACCGG AATTGGTCCA CCGGCACCGG ATAATTTCGA TTATCTTCAT
1051 GAAGTTGGGT GTAAGCTGGC TCATTTAGCT GAGGCGATTC ACGTTGAGTT
1101 TGAGTACAGA GGATTTGTGG CTAACACTTT AGCTGATCTT GATGCTTCGA
1151 TGCTTGAGCT TAGACCAAGT GAGATTGAAT CTGTTGCGGT TAACTCTGTT
1201 TTCGAGCTTC ACAAGCTCTT GGGACGACCT GGTGCGATCG ATAAGGTTCT
1251 TGGTGTGGTG AATCAGATTA AACCGGAGAT TTTCACTGTG GTTGAGCAGG
1301 AATCGAACCA TAATAGTCCG ATTTTCTTAG ATCGGTTTAC TGAGTCGTTG
1351 CATTATTACT CGACGTTGTT TGACTCGTTG GAAGGTGTAC CGAGTGGTCA
1401 AGACAAGGTC ATGTCGGAGG TTTACTTGGG TAAACAGATC TGCAACGTTG
1451 TGGCTTGTGA TGGACCTGAC CGAGTTGAGC GTCATGAAAC GTTGAGTCAG
1501 TGGAGGAACC GGTTCGGGTC TGCTGGGTTT GCGGCTGCAC ATATTGGTTC
1551 GAATGCGTTT AAGCAAGCGA GTATGCTTTT GGCTCTGTTC AACGGCGGTG
1601 AGGGTTATCG GCTGGAGGAG AGTGACGGCT GTCTCATGTT GCG
```

Figure 6(b)

```
  1   MKRDHHHHHQ  DKKTMMMNEE  DDGNGMDVAQ  KLEQLEVMMS  NVQEDDLSQL
 51   ATETVHYNPA  ELYTWLDSML  TDLNPPSSNA  EYDLKAIPGD  AILNQFAIDS
101   ASSSNQGGGG  DTYTTNKRLK  CSNGVVETTT  ATAESTRHVV  LVDSQENGVR
151   LVHALLACAE  AVQKENLTVA  EALVKQIGFL  AVSQIGAMRK  VATYFAEALA
201   RRIYRLSPSQ  SPIDHSLSDT  L*
```

Figure 6(c)

```
   1 TAGAAGTGGT AGTGGACTCA AAAAACAAAT CCTAAGCAGT CCTAACCGAT
  51 CCCCGAAGCT AAAGATTCTT CACCTTCCCA AATAAAGCAA AACCTAGATC
 101 CGACATTGAA GGAAAAACCT TTTAGATCCA TCTCTGAAAA AAAACCAACC
 151 ATGAAGAGAG ATCATCATCA TCATCATCAA GATAAGAAGA CTATGATGAT
 201 GAATGAAGAA GACGACGGTA ACGGCATGGA TGTTGCTCAG AAACTCGAGC
 251 AGCTTGAAGT TATGATGTCT AATGTTCAAG AAGACGATCT TTCTCAACTC
 301 GCTACTGAGA CTGTTCACTA TAATCCGGCG GAGCTTTACA CGTGGCTTGA
 351 TTCTATGCTC ACCGACCTTA ATCCTCCGTC GTCTAACGCC GAGTACGATC
 401 TTAAAGCTAT TCCCGGTGAC GCGATTCTCA ATCAGTTCGC TATCGATTCG
 451 GCTTCTTCGT CTAACCAAGG CGGCGGAGGA GATACGTATA CTACAAACAA
 501 GCGGTTGAAA TGCTCAAACG GCGTCGTGGA AACCACCACA GCGACGGCTG
 551 AGTCAACTCG GCATGTTGTC CTGGTTGACT CGCAGGAGAA CGTGTGCGT
 601 CTCGTTCACG CGCTTTTGGC TTGCGCTGAA GCTGTTCAGA AGGAGAATCT
 651 GACTGTGGCG GAAGCTCTGG TGAAGCAAAT CGGATTCTTA GCTGTTTCTC
 701 AAATCGGAGC TATGAGAAAA GTCGCTACTT ACTTCGCCGA AGCTCTCGCG
 751 CGGCGGATTT ACCGTCTCTC TCCGTCGCAG AGTCCAATCG ACCACTCTCT
 801 CTCCGATACT CTTCAGATGC ACTTCTACGA GACTTGTCCT TATCTCAAGT
 851 TCGCTCACTT CACGGCGAAT CAAGCGATTC TCGAAGCTTT TCAAGGGAAG
 901 AAAAGAGTTC ATGTCATTGA TTCTCTATGA GTCAAGGTCT TCAATGGCCG
 951 GCGCTTATGC AGGCTCTTGC GCTTCGACCT GGTGGTCCTC CTGTTTTCCG
1001 GTTAACCGGA ATTGGTCCAC CGGCACCGGA TAATTTCGAT TATCTTCATG
1051 AAGTTGGGTG TAAGCTGGCT CATTTAGCTG AGGCGATTCA CGTTGAGTTT
1101 GAGTACAGAG GATTTGTGGC TAACACTTTA GCTGATCTTG ATGCTTCGAT
1151 GCTTGAGCTT AGACCAAGTG AGATTGAATC TGTTGCGGTT AACTCTGTTT
1201 TCGAGCTTCA CAAGCTCTTG GGACGACCTG GTGCGATCGA TAAGGTTCTT
1251 GGTGTGGTGA ATCAGATTAA ACCGGAGATT TTCACTGTGG TTGAGCAGGA
1301 ATCGAACCAT AATAGTCCGA TTTTCTTAGA TCGGTTTACT GAGTCGTTGC
1351 ATTATTACTC GACGTTGTTT GACTCGTTGG AAGGTGTACC GAGTGGTCAA
1401 GACAAGGTCA TGTCGGAGGT TTACTTGGGT AAACAGATCT GCAACGTTGT
1451 GGCTTGTGAT GGACCTGACC GAGTTGAGCG TCATCAAACG TTGAGTCAGT
1501 GGAGCAACCG GTTCGGGTCT GCTGGGTTTG CGGCTGCACA TATTGGTTCG
1551 AATGCGTTTA AGCAAGCGAG TATGCTTTTG GCTCTGTTCA ACGGCGGTCA
1601 GGGTTATCGG GTGGAGGAGA GTGACGGCTG TCTCATGTTG GG
```

Figure 6(d)

```
  1  MKRDHHHHHQ DKKTMMMNEE DDGNGMDVAQ KLEQLEVMMS NVQEDDLSQL
 51  ATETVHYNPA ELYTWLDSML TDLNPPSSNA EYDLKAIPGD AILNQFAIDS
101  ASSSNQGGGG DTYTTNKRLK CSNGVVETTT ATAESTRHVV LVDSQENGVR
151  LVHALLACAE AVQKENLTVA EALVKQIGFL AVSQIGAMRK VATYFAEALA
201  RRIYRLSPSQ SPIDHSLSDT LQMHFYETCP YLKFAHFTAN QAILEAFQGK
251  KRVHVIDSL*
```

Figure 6(e)

```
   1  TAGAAGTGGT AGTGGAGTGA AAAAACAAAT CCTAAGCAGT CCTAACCGAT
  51  CCCCGAAGCT AAAGATTCTT CACCTTCCCA AATAAAGCAA AACCTAGATC
 101  CGACATTGAA GGAAAAACCT TTTAGATCCA TCTCTGAAAA AAAACCAACC
 151  ATGAAGAGAG ATCATCATCA TCATCATCAA GATAAGAAGA CTATGATGAT
 201  GAATGAAGAA GACGACGGTA ACGGCATGGA TGTTGCTCAG AAACTCGAGC
 251  AGCTTGAAGT TATGATGTCT AATGTTCAAG AAGACGATCT TTCTCAACTC
 301  GCTACTGAGA CTGTTCACTA TAATCCGGCG GAGCTTTACA CGTGGCTTGA
 351  TTCTATGCTC ACCGACCTTA ATCCTCCGTC GTCTAACGCC GAGTACGATC
 401  TTAAAGCTAT TCCCGGTGAC GCGATTCTCA ATCAGTTCGC TATCGATTCG
 451  GCTTCTTCGT CTAACCAAGG CGGCGGAGGA GATACGTATA CTACAAACAA
 501  GCGGTTGAAA TGCTCAAACG GCGTCGTGGA AACCACCACA GCGACGGCTG
 551  AGTCAACTCG GCATGTTGTC CTGGTTGACT CGCAGGAGAA CGGTGTGCGT
 601  CTCGTTCACG CGCTTTTGGC TTGCGCTGAA GCTGTTCAGA AGGAGAATCT
 651  GACTGTGGCG GAAGCTCTGG TGAAGCAAAT CGGATTCTTA GCTGTTTCTC
 701  AAATCGGAGC TATGAGAAAA GTCGCTACTT ACTTCGCCGA AGCTCTCGCG
 751  CGGCGGATTT ACCGTCTCTC TCCGTCGCAG AGTCCAATCG ACCACTCTCT
 801  CTCCGATACT CTTCAGATGC ACTTCTACGA GACTTGTCCT TATCTCAAGT
 851  TCGCTCACTT CACGGCGAAT CAAGCGATTC TCGAAGCTTT TCAAGGGAAG
 901  AAAAGAGTTC ATGTCATTGA TTTCTCTATG AGTCAAGGTC TTGGGCGCTT
 951  ATGCAGGCTC TTGCGCTTCG ACCTGGTGGT CCTCCTGTTT TCCGGTTAAC
1001  CGGAATTGGT CCACCGGCAC CGGATAATTT CGATTATCTT CATGAAGTTG
1051  GGTGTAAGCT GGCTCATTTA GCTGAGGCGA TTCACGTTGA GTTTGAGTAC
1101  AGAGGATTTG TGGCTAACAC TTTAGCTGAT CTTGATGCTT CGATGCTTGA
1151  GCTTAGACCA AGTGAGATTG AATCTGTTGC GGTTAACTCT GTTTTCGAGC
1201  TTCACAAGCT CTTGGGACGA CCTGGTGCGA TCGATAAGGT TCTTGGTGTG
1251  GTGAATCAGA TTAAACCGGA GATTTTCACT GTGGTTGAGC AGGAATCGAA
1301  CCATAATAGT CCGATTTTCT TAGATCGGTT TACTGAGTCG TTGCATTATT
1351  ACTCGACGTT GTTTGACTCG TTGGAAGGTG TACCGAGTGG TCAAGACAAG
1401  GTCATGTCGG AGGTTTACTT GGGTAAACAG ATCTGCAACG TTGTGGCTTG
1451  TGATGGACCT GACCGAGTTG AGCGTCATGA AACGTTGAGT CAGTGGAGGA
1501  ACCGGTTCGG GTCTGCTGGG TTTGCGGCTG CACATATTGG TTCGAATGCG
1551  TTTAAGCAAG CGAGTATGCT TTTGGCTCTG TTCAACGGCG GTGAGGGTTA
1601  TCGGGTGGAG GAGAGTGACG GCTGTCTCAT GTTGGG
```

Figure 6(f)

```
  1  MKRDHHHHHQ DKKTMMMNEE DDGNGMDVAQ KLEQLEVMMS NVQEDDLSQL

51  ATETVHYNPA ELYTWLDSML TDLNPPSSNA EYDLKAIPGD AILNQFAIDS

101  ASSSNQGGGG DTYTTNKRLK CSNGVVETTT ATAESTRHVV LVDSQENGVR

151  LVHALLACAE AVQKENLTVA EALVKQIGFL AVSQIGAMRK VATYFAEALA

201  RRIYRLSPSQ SPIDHSLSDT LQMHFYETCP YLKFAHFTAN QAILEAFQGK

251  KRVHVIDFSM SQGLGRLCRL LRFDLVVLLF SG*
```

Figure 6(g)

```
   1  TAGAAGTGGT AGTGGAGTGA AAAAACAAAT CCTAAGCAGT CCTAACCGAT
  51  CCCCGAAGCT AAAGATTCTT CACCTTCCCA AATAAAGCAA AACCTAGATC
 101  CGACATTGAA GGAAAAACCT TTTAGATCCA TCTCTGAAAA AAAACCAACC
 151  ATGAAGAGAG ATCATCATCA TCATCATCAA GATAAGAAGA CTATGATGAT
 201  GAATGAAGAA GACGACGGTA ACGGCATGGA TGTTGCTCAG AAACTCGAGC
 251  AGCTTGAAGT TATGATGTCT AATGTTCAAG AAGACGATCT TTCTCAACTC
 301  GCTACTGAGA CTGTTCACTA TAATCCGGCG GAGCTTTACA CGTGGCTTGA
 351  TTCTATGCTC ACCGACCTTA ATCCTCCGTC GTCTAACGCC GAGTACGATC
 401  TTAAAGCTAT TCCCGGTGAC GCGATTCTCA ATCAGTTCGC TATCGATTCG
 451  GCTTCTTCGT CTAACCAAGG CGGCGGAGGA GATACGTATA CTACAAACAA
 501  GCGGTTGAAA TGCTCAAACG GCGTCGTGGA AACCACCACA GCGACGGCTG
 551  AGTCAACTCG GCATGTGTCC TGGTTGACTC GCAGGAGAAC GGTGTGCGTC
 601  TCGTTCACGC GCTTTTGGCT TGCGCTGAAG CTGTTCAGAA GGAGAATCTG
 651  ACTGTGGCGG AAGCTCTGGT GAAGCAAATC GGATTCTTAG CTGTTTCTCA
 701  AATCGGAGCT ATGAGAAAAG TCGCTACTTA CTTCGCCGAA GCTCTCGCGC
 751  GGCGGATTTA CCGTCTCTCT CCGTCGCAGA GTCCAATCGA CCACTCTCTC
 801  TCCGATACTC TTCAGATGCA CTTCTACGAG ACTTGTCCTT ATCTCAAGTT
 851  CGCTCACTTC ACGGCGAATC AAGCGATTCT CGAAGCTTTT CAAGGGAAGA
 901  AAAGAGTTCA TGTCATTGAT TTCTCTATGA GTCAAGGTCT TCAATGGCCG
 951  GCGCTTATGC AGGCTCTTGC GCTTCGACCT GGTGGTCCTC CTGTTTTCCG
1001  GTTAACCGGA ATTGGTCCAC CGGCACCGGA TAATTTCGAT TATCTTCATG
1051  AAGTTGGGTG TAAGCTGGCT CATTTAGCTG AGGCGATTCA CGTTGAGTTT
1101  GAGTACAGAG GATTTGTGGC TAACACTTTA GCTGATCTTG ATGCTTCGAT
1151  GCTTGAGCTT AGACCAAGTG AGATTGAATC TGTTGCGGTT AACTCTGTTT
1201  TCGAGCTTCA CAAGCTCTTG GGACGACCTG GTGCGATCGA TAAGGTTCTT
1251  GGTGTGGTGA ATCAGATTAA ACCGGAGATT TTCACTGTGG TTGAGCAGGA
1301  ATCGAACCAT AATAGTCCGA TTTTCTTAGA TCGGTTTACT GAGTCGTTGC
1351  ATTATTACTC GACGTTGTTT GACTCGTTGG AAGGTGTACC GAGTGGTCAA
1401  GACAAGGTCA TGTCGGAGGT TTACTTGGGT AAACAGATCT GCAACGTTGT
1451  GGCTTGTGAT GGACCTGACC GAGTTGAGCG TCATGAAACG TTGAGTCAGT
1501  GGAGGAACCG GTTCGGGTCT GCTGGGTTTG CGGCTGCACA TATTGGTTCG
1551  AATGCGTTTA AGCAAGCGAG TATGCTTTTG GCTCTGTTCA ACGGCGGTGA
1601  GCGTTATCGG GTGGAGGAGA GTGACGGCTG TCTCATGTTG GG
```

Figure 6(h)

```
  1  MKRDHHHHHQ DKKTMMMNEE DDGNGMDVAQ KLEQLEVMMS NVQEDDLSQL
 51  ATETVHYNPA ELYTWLDSML TDLNPPSSNA EYDLKAIPGD AILNQFAIDS
101  ASSSNQGGGG DTYTTNKRLK CSNGVVETTT ATAESTRHVS WLTRRRTVCV
151  SFTRFWLALK LFRRRI*
```

NUCLEIC ACID ENCODING GAI GENE OF ARABIDOPSIS THALIANA

This application is a continuation of application Ser. No. 09/117,853, filed Aug. 12, 1998 and now U.S. Pat. No. 6,307,126, which is a 371 of PCT/GB97/00390, filed Feb. 12, 1997, the entire content of which is hereby incorporated by reference in this application.

This invention relates to the genetic control of growth and/or development of plants and the cloning and expression of genes involved therein. More particularly, the invention relates to the cloning and expression of the GAI gene of *Arabidopsis thaliana*, and homologues from other species, and use of the genes in plants.

BACKGROUND OF THE INVENTION

An understanding of the genetic mechanisms which influence growth and development of plants, including flowering, provides a means for altering the characteristics of a target plant. Species for which manipulation of growth and/or development characteristics may be advantageous includes all crops, with important examples being the cereals, rice and maize, probably the most agronomically important in warmer climatic zones, and wheat, barley, oats and rye in more temperate climates. Important crops for seed products are oil seed rape and canola, sugar beet, maize, sunflower, soyabean and sorghum. Many crops which are harvested for their roots are, of course, grown annually from seed and the production of seed of any kind is very dependent upon the ability of the plant to flower, to be pollinated and to set seed. In horticulture, control of the timing of growth and development, including flowering, is important. Horticultural plants whose flowering may be controlled include lettuce, endive and vegetable brassicas including cabbage, broccoli and cauliflower, and carnations and geraniums. Dwarf plants on the one hand and over-size, taller plants on the other may be advantageous and/or desirable in various horticultural and agricultural contexts.

*Arabidopsis thaliana* is a favourite of plant geneticists as a model organism. Because it has a small, well-characterized genome, is relatively easily transformed and regenerated and has a rapid growing cycle, *Arabidopsis* is an ideal model plant in which to study growth and development and its control.

Many plant growth and developmental processes are regulated by specific members of a family of tetracyclic diterpenoid growth factors known as gibberellins (GA)[1]. The gai mutation of *Arabidopsis* confers a dwarf phenotype and a dramatic reduction in GA-responsiveness[2-9]. Here we report the molecular cloning of gai via Ds transposon mutagenesis.

The phenotype conferred by the Ds insertion allele confirms that gai is a gain-of-function mutation, and that the wild-type allele (GAI) is dispensable[5,6]. GAI encodes a novel polypeptide (GAI) of 532 amino acid residues, of which a 17 amino acid domain is missing in the gai mutant polypeptide. This result is consistent with GAI acting as a plant growth repressor whose activity is antagonized by GA. Though we are not to be bound by any particular theory, gai may repress growth constitutively because it lacks the domain that interacts with the GA signal. Thus according to this model GA regulates plant growth by de-repression.

gai is a dominant, gain-of-function mutation, which confers a dark-green, dwarf phenotype, and interferes with GA reception or subsequent signal-transduction[2-9]. Dominant mutations conferring similar phenotypes are known in other plant species, including maize[10-12] and wheat[13]. The latter are especially important because they are the basis of the high-yielding, semi-dwarf wheat varieties of the 'green revolution'[14]. The increased yield of these varieties is due to an increased grain production per ear, and superior straw strength. The shorter, stronger straw greatly reduces the losses resulting from lodging, that is flattening of standing wheat plants by rain/wind. We set out to clone gai from *Arabidopsis* because of its importance to the understanding of GA signal-transduction, and because of the potential for use of GA-insensitivity in the development of wheat and other crops such as oil-seed rape and rice which may show improvement as great as that already seen in wheat.

SUMMARY OF THE INVENTION

According to a first aspect of the present invention there is provided a nucleic acid molecule comprising a nucleotide sequence encoding a polypeptide with GAI function. The term "GAI function" indicates ability to influence the phenotype of a plant like the GAI gene of *Arabidopsis thaliana*. "GAI function" may be observed phenotypically in a plant as inhibition, suppression, repression or reduction of plant growth which inhibition, suppression, repression or reduction is antagonised by GA. GAI expression tends to confer a dwarf phenotype on a plant which is antagonised by GA. Overexpression in a plant from a nucleotide sequence encoding a polypeptide with GAI function may be used to confer a dwarf phenotype on a plant which is correctable by treatment with GA.

Also according to an aspect of the present invention there is provided a nucleic acid molecule comprising a nucleotide sequence encoding a polypeptide with ability to confer a gai mutant phenotype upon expression. gai mutant plants are dwarfed compared with wild-type, the dwarfing being GA-insensitive.

By gibberellin or GA is meant a diterpenoid molecule with the basic carbon-ring structure shown in FIG. 1 and possessing biological activity, i.e. we refer to biologically active gibberellins.

Biological activity may be defined by one or more of stimulation of cell elongation, leaf senescence or elicitation of the cereal aleurone α-amylase response. There are many standard assays available in the art, a positive result in any one or more of which signals a test gibberellin as biologically active[28,29,30].

Assays available in the art include the lettuce hypocotyl assay, cucumber hypocotyl assay, and oat first leaf assay, all of which determine biological activity on the basis of ability of an applied gibberellin to cause elongation of the respective tissue. Preferred assays are those in which the test composition is applied to a gibberellin-deficient plant. Such preferred assays include treatment of dwarf GA-deficient *Arabidopsis* to determine growth, the dwarf pea assay, in which internode elongation is determined, the Tanginbozu dwarf rice assay, in which elongation of leaf sheath is determined, and the d5-maize assay, also in which elongation of leaf sheath is determined. The elongation bioassays measure the effects of general cell elongation in the respective organs and are not restricted to particular cell types.

Further available assays include the dock (Rumex) leaf senescence assay and the cereal aleurone α-amylase assay. Aleurone cells which surround the endosperm in grain secrete α-amylase on germination, which digests starch to produce sugars then used by the growing plant. The enzyme production is controlled by GA. Isolated aleurone cells given biologically active GA secrete α-amylase whose activity can then be assayed, for example by measurement of degradation of starch.

Structural features important for high biological activity (exhibited by $GA_1$, $GA_2$, $GA_4$ and $GA_7$) are a carboxyl group on C-6 of B-ring; C-19, C-10 lactone; and β-hydroxylation at C-3. β-hydroxylation at C-2 causes inactivity (exhibited by $GA_8$, $GA_{29}$, $GA_{34}$ and $GA_{51}$). gai mutants do not respond to GA treatment, e.g. treatment with $GA_1$, $GA_3$ or $GA_4$.

Treatment with GA is preferably by spraying with aqueous solution, for example spraying with $10^{-4}M$ $GA_3$ or $GA_4$ in aqueous solution, perhaps weekly or more frequently, and may be by placing droplets on plants rather than spraying. GA may be applied dissolved in an organic solvent such as ethanol or acetone, because it is more soluble in these than in water, but this is not preferred because these solvents have a tendency to damage plants. If an organic solvent is to be used, suitable formulations include 24 ηl of 0.6, 4.0 or 300 mM $GA_3$ or $GA_4$ dissolved in 80% ethanol. Plants, e.g. Arabidopsis, may be grown on a medium containing GA, such as tissue culture medium (GM) solidified with agar and containing supplementary GA.

Nucleic acid according to the present invention may have the sequence of a wild-type GAI gene of Arabidopsis thaliana, or be a mutant, derivative, variant or allele of the sequence provided. Preferred mutants, derivatives, variants and alleles are those which encode a protein which retains a functional characteristic of the protein encoded by the wild-type gene, especially the ability for plant growth inhibition, which inhibition is antagonised by GA, or ability to confer on a plant one or more other characteristics responsive to GA treatment of the plant. Other preferred mutants, derivatives, variants and alleles encode a protein which confers a gai mutant phenotype, that is to say reduced plant growth which reduction is insensitive to GA, i.e. not overcome by GA treatment. Changes to a sequence, to produce a mutant, variant or derivative, may be by one or more of addition, insertion, deletion or substitution of one or more nucleotides in the nucleic acid, leading to the addition, insertion, deletion or substitution of one or more amino acids in the encoded polypeptide. Of course, changes to the nucleic acid which make no difference to the encoded amino acid sequence are included.

A preferred nucleotide sequence for a GAI gene is one which encodes amino acid sequence shown in FIG. 4 (SEQ ID NO:2). especially a coding sequence shown in FIG. 3 (SEQ ID NO:1). A preferred gai mutant lacks part or all of the 17 amino acid sequence underlined in FIG. 4.

The present invention also provides a nucleic acid construct or vector which comprises nucleic acid with any one of the provided sequences, preferably a construct or vector from which polypeptide encoded by the nucleic acid sequence can be expressed. The construct or vector is preferably suitable for transformation into a plant cell. The invention further encompasses a host cell transformed with such a construct or vector, especially a plant cell. Thus, a host cell, such as a plant cell, comprising nucleic acid according to the present invention is provided. Within the cell, the nucleic acid may be incorporated within the chromosome. There may be more than one heterologous nucleotide sequence per haploid genome. This, for example, enables increased expression of the gene product compared with endogenous levels, as discussed below.

A construct or vector comprising nucleic acid according to the present invention need not include a promoter or other regulatory sequence, particularly if the vector is to be used to introduce the nucleic acid into cells for recombination into the genome. However, in one aspect the present invention provides a nucleic acid construct comprising a GAI or gai coding sequence (which includes homologues from other than Arabidopsis thaliana) joined to a regulatory sequence for control of expression, the regulatory sequence being other than that naturally fused to the coding sequence and preferably of or derived from another gene.

Nucleic acid molecules and vectors according to the present invention may be as an isolate, provided isolated from their natural environment, in substantially pure or homogeneous form, or free or substantially free of nucleic acid or genes of the species of interest or origin other than the sequence encoding a polypeptide able to influence growth and/or development, which may include flowering, eg in Arabidopsis thaliana nucleic acid other than the GAI coding sequence. The term "nucleic acid isolate" encompasses wholly or partially synthetic nucleic acid.

Nucleic acid may of course be double- or single-stranded, cDNA or genomic DNA, RNA, wholly or partially synthetic, as appropriate. Of course, where nucleic acid according to the invention includes RNA, reference to the sequence shown should be construed as reference to the RNA equivalent, with U substituted for T.

The present invention also encompasses the expression product of any of the nucleic acid sequences disclosed and methods of making the expression product by expression from encoding nucleic acid therefor under suitable conditions in suitable host cells. Those skilled in the art are well able to construct vectors and design protocols for expression and recovery of products of recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, Molecular Cloning: a Laboratory Manual: 2nd edition, Sambrook et al, 1989, Cold Spring Harbor Laboratory Press. Transformation procedures depend on the host used, but are well known. Many known techniques and protocols for manipulation of nucleic acid, for example in preparation of nucleic acid constructs, mutagenesis, sequencing, introduction of DNA into cells and gene expression, and analysis of proteins, are described in detail in Protocols in Molecular Biology, Second Edition, Ausubel et al. eds., John Wiley & Sons, 1992. Specific procedures and vectors previously used with wide success upon plants are described by Bevan, Nucl. Acids Res. (1984) 12, 8711–8721), and Guerineau and Mullineaux, (1993) Plant transformation and expression vectors. In: Plant Molecular Biology Labfax (Croy RRD ed) Oxford, BIOS Scientific Publishers, pp 121–148. The disclosures of Sambrook et al. and Ausubel et al. and all other documents mentioned herein are incorporated herein by reference.

Since the GAI amino acid sequence of Arabidopsis shown in FIG. 4 (SEQ ID NO:2) includes 5 consecutive histidines close to its N-terminus, substantial purification of GAI or gai may be achieved using Ni-NTA resin available from QIAGEN Inc. (USA) and DIAGEN GmbH (Germany). See Janknecht et al[31] and EP-A-0253303 and EP-A-0282042. Ni-NTA resin has high affinity for proteins with consecutive histidines close to the N- or C-terminus of the protein and so may be used to purifiy GAI or gai proteins from plants, plant parts or extracts or from recombinant organisms such as yeast or bacteria, e.g. E. coli, expressing the protein.

Purified GAI protein, e.g. produced recombinantly by expression from encoding nucleic acid therefor, may be used to raise antibodies employing techniques which are standard in the art. Antibodies and polypeptides comprising antigen-binding fragments of antibodies may be used in identifying homologues from other species as discussed further below.

Methods of producing antibodies include immunising a mammal (eg human, mouse, rat, rabbit, horse, goat, sheep or monkey) with the protein or a fragment thereof. Antibodies may be obtained from immunised animals using any of a variety of techniques known in the art, and might be screened, preferably using binding of antibody to antigen of interest. For instance, Western blotting techniques or immunoprecipitation may be used (Armitage et al, 1992, Nature 357: 80–82). Antibodies may be polyclonal or monoclonal.

As an alternative or supplement to immunising a mammal, antibodies with appropriate binding specificty may be obtained from a recombinantly produced library of expressed immunoglobulin variable domains, eg using lambda bacteriophage or filamentous bacteriophage which display functional immunoglobulin binding domains on their surfaces; for instance see WO92/01047.

Antibodies raised to a GAI, or gai, polypeptide can be used in the identification and/or isolation of homologous polypeptides, and then the encoding genes. Thus, the present invention provides a method of identifying or isolating a polypeptide with GAI function or ability to confer a gai mutant phenotype, comprising screening candidate polypeptides with a polypeptide comprising the antigen-binding domain of an antibody (for example whole antibody or a fragment thereof) which is able to bind an *Arabidopsis* GAI or gai polypeptide, or preferably has binding specificity for such a polypeptide, such as having the amino acid sequence shown in FIG. 4 (SEQ ID NO:2).

Candidate polypeptides for screening may for instance be the products of an expression library created using nucleic acid derived from an plant of interest, or may be the product of a purification process from a natural source.

A polypeptide found to bind the antibody may be isolated and then may be subject to amino acid sequencing. Any suitable technique may be used to sequence the polypeptide either wholly or partially (for instance a fragment of the polypeptide may be sequenced). Amino acid sequence information may be used in obtaining nucleic acid encoding the polypeptide, for instance by designing one or more oligonucleotides (e.g. a degenerate pool of oligonucleotides) for use as probes or primers in hybridisation to candidate nucleic acid, as discussed further below.

A further aspect of the present invention provides a method of identifying and cloning GAI homologues from plant species other than *Arabidopsis thaliana* which method employs a nucleotide sequence derived from that shown in FIG. 3 (SEQ ID NO:1). Sequences derived from these may themselves be used in identifying and in cloning other sequences. The nucleotide sequence information provided herein, or any part thereof, may be used in a data-base search to find homologous sequences, expression products of which can be tested for GAI function. Alternatively, nucleic acid libraries may be screened using techniques well known to those skilled in the art and homologous sequences thereby identified then tested.

For instance, the present invention also provides a method of identifying and/or isolating a GAI or gai homologue gene, comprising probing candidate (or "target") nucleic acid with nucleic acid which encodes a polypeptide with GAI function or a fragment or mutant, derivative or allele thereof. The candidate nucleic acid (which may be, for instance, cDNA or genomic DNA) may be derived from any cell or organism which may contain or is suspected of containing nucleic acid encoding such a homologue.

In a preferred embodiment of this aspect of the present invention, the nucleic acid used for probing of candidate nucleic acid encodes an amino acid sequence shown in FIG. 4 (SEQ ID NO:2), a sequence complementary to a coding sequence, or a fragment of any of these, most preferably comprising a nucleotide, sequence shown in FIG. 3 (SEQ ID NO:1).

Alternatively, as discussed, a probe may be designed using amino acid sequence information obtained by sequencing a polypeptide identified as being able to be bound by an antigen-binding domain of an antibody which is able to bind a GAI or gai polypeptide such as one with the amino acid sequence shown in FIG. 4 (SEQ ID NO:2).

Preferred conditions for probing are those which are stringent enough for there to be a simple pattern with a small number of hybridizations identified as positive which can be investigated further. It is well known in the art to increase stringency of hybridisation gradually until only a few positive clones remain.

As an alternative to probing, though still employing nucleic acid hybridisation, oligonucleotides designed to amplify DNA sequences from GAI genes may be used in PCR or other methods involving amplification of nucleic acid, using routine procedures. See for instance "PCR protocols; A Guide to Methods and Applications", Eds. Innis et al, 1990, Academic Press, New York.

Preferred amino acid sequences suitable for use in the design of probes or PCR primers are sequences conserved (completely, substantially or partly) between GAI genes.

On the basis of amino acid sequence information, oligonucleotide probes or primers may be designed, taking into account the degeneracy of the genetic code, and, where appropriate, codon usage of the organism from the candidate nucleic acid is derived.

The present invention also extends to nucleic acid encoding a GAI homologue obtained using a nucleotide sequence derived from that shown in FIG. 3 (SEQ ID NO:1).

Also included within the scope of the present invention are nucleic acid molecules which encode amino acid sequences which are homologues of the polypeptide encoded by GAI of *Arabidopsis thaliana*. A homologue may be from a species other than *Arabidopsis thaliana*.

Homology may be at the nucleotide sequence and/or amino acid sequence level. Preferably, the nucleic acid and/or amino acid sequence shares homology with the sequence encoded by the nucleotide sequence of FIG. 3 (SEQ ID NO:1), preferably at least about 50%, or 60%, or 70%, or 80% homology, most preferably at least 90% or 95% homology. Nuleic acid encoding such a polypeptide may preferably share with the *Arabidopsis thaliana* GAI gene the ability to confer a particular phenotype on expression in a plant, preferably a phenotype which is GA responsive (i.e. there is a change in a characteristic of the plant on treatment with GA), such as the ability to inhibit plant growth where the inhibition is antagonised by GA. As noted, GAI expression in a plant may affect one or more other characteristics of the plant. A preferred characteristic that may be shared with the *Arabidopsis thaliana* GAI gene is the ability to complement a GAI null mutant phenotype in a plant such as *Arabidopsis thaliana*, such phenotype being resistance to the dwarfing effect of paclobutrazol.

Some preferred embodiments of polypeptides according to the present invention (encoded by nucleic acid embodiments according to the present invention) include the 17 amino acid sequence which is underlined in FIG. 4 or a contiguous sequence of amino acids residues with at least about 10 residues with similarity or identity with the respective corresponding residue (in terms of position) in 17 amino acids which are underlined in FIG. 4, more preferably, 11, 12, 13, 14, 15, 16 or 17 such residues.

As is well-understood, homology at the amino acid level is generally in terms of amino acid similarity or identity. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Similarity may be as defined and determined by the TBLASTN program, of Altschul et al. (1990) *J. Mol. Biol.* 215: 403–10, which is in standard use in the art. Homology may be over the full-length of the GAI sequence of FIG. 4 (SEQ ID NO:2), or may more preferably be over a contiguous sequence of 17 amino acids, compared with the 17 amino acids underlined in FIG. 4, or a longer sequence, e.g. about 20, 25, 30, 40, 50 or more amino acids, compared with the amino acid sequence of FIG. 4 (SEQ ID NO:2) and preferably including the underlined 17 amino acids.

At the nucleic acid level, homology may be over the full-length or more preferably by comparison with the 51 nucleotide coding sequence within the sequence of FIG. 3 (SEQ ID NO:1) and encoding the 17 amino acid sequence underlined in FIG. 4, or a longer sequence, e.g. about, 60, 70, 80, 90, 100, 120, 150 or more nucleotides and preferably includeing the 51 nucleotide of FIG. 3 (SEQ ID NO:1) which encodes the underlined 17 amino acid sequence of FIG. 4.

Homologues to gai mutants are also provided by the present invention. These may be mutants where the wild-type includes the 17 amino acids underlined in FIG. 4, or a contiguous sequence of 17 amino acids with at least about 10 (more preferably, 11, 12, 13, 14, 15, 16 or 17) which have similarity or identity with the corresponding residue in the 17 amino acid sequence underlined in FIG. 4, but the mutant does not. Nucleic acid encoding such mutant polypeptides may on expression in a plant confer a phenotype which is insensitive or unresponsive to treatment of the plant with GA, that is a mutant phenotype which is not overcome or there is no reversion to wild-type phenotype on treatment of the plant with GA (though there may be some response in the plant on provision or depletion of GA).

A further aspect of the present invention provides a nucleic acid isolate having a nucleotide sequence encoding a polypeptide which includes an amino acid sequence which is a mutant, allele, derivative or variant sequence of the GAI amino acid sequence of the species *Arabidopsis thaliana* shown in FIG. 4 (SEQ ID NO:2), or is a homologue of another species or a mutant, allele, derivative or variant thereof, wherein said mutant, allele, derivative, variant or homologue differs from the amino acid sequence shown in FIG. 4 (SEQ ID NO:2) by way of insertion, deletion, addition and/or substitution of one or more amino acids, as obtainable by producing transgenic plants by transforming plants which have a GAI null mutant phenotype, which phenotype is resistance to the dwarfing effect of paclobutrazol, with test nucleic acid, causing or allowing expression from test nucleic acid within the transgenic plants, screening the transgenic plants for those exhibiting complementation of the GAI null mutant phenotype to identify test nucleic acid able to complement the GAI null mutant, deleting from nucleic acid so identified as being able to complement the GAI null mutant a nucleotide sequence encoding the 17 amino acid sequence underlined in FIG. 4 or a contiguous 17 amino acid sequence in which at least 10 residues have similarity or identity with the respective amino acid in the corresponding position in the 17 amino acid sequence underlined in FIG. 4, more preferably 11, 12, 13, 14, 15, 16 or 17.

GAI and gai gene homologues may be identified from economically important: monocotyledonous crop plants such as wheat, rice and maize. Although genes encoding the same protein in monocotyledonous and dicotyledonous plants show relatively little homology at the nucleotide level, amino acid sequences are conserved.

In public sequence databases we recently identified several EST sequences that were obtained in random sequencing programmes and share homology with GAI. Table 2 gives details, showing that homologous sequences have been found in various species, including *Zea Mays* (maize), *O. Sativa* (rice), and *Brassica napus* (rape) By sequencing, study of expression patterns and examining the effect of altering their expression, GAI gene homologues, carrying out a similar function in other plants, are obtainable. Of course, novel uses and mutants, derivatives and alleles of these sequences are included within the scope of the various aspects of the present invention in the same terms as discussed above for the *Arabidopsis thaliana* gene.

A cell containing nucleic acid of the present invention represents a further aspect of the invention, particularly a plant cell, or a bacterial cell.

The cell may comprise the nucleic acid encoding the enzyme by virtue of introduction into the cell or an ancestor thereof of the nucleic acid, e.g. by transformation using any suitable technique available to those skilled in the art.

Also according to the invention there is provided a plant cell having incorporated into its genome nucleic acid as disclosed. The present invention also provides a plant comprising such a plant cell.

Also according to the invention there is provided a plant cell having incorporated into its genome a sequence of nucleotides as provided by the present invention, under operative control of a regulatory sequence for control of expression. A further aspect of the present invention provides a method of making such a plant cell involving introduction of a vector comprising the sequence of nucleotides into a plant cell and causing or allowing recombination between the vector and the plant cell genome to introduce the sequence of nucleotides into the genome.

A plant according to the present invention may be one which does not breed true in one or more properties. Plant varieties may be excluded, particularly registrable plant varieties according to Plant Breeders' Rights. It is noted that a plant need not be considered a "plant variety" simply because it contains stably within its genome a transgene, introduced into a cell of the plant or an ancestor thereof.

In addition to a plant, the present invention provides any clone of such a plant, seed, selfed or hybrid progeny and descendants, and any part of any of these, such as cuttings, seed. The invention provides any plant propagule, that is any part which may be used in reproduction or propagation, sexual or asexual, including cuttings, seed and so on. Also encompassed by the invention is a plant which is a sexually or asexually propagated off-spring, clone or descendant of such a plant, or any part or propagule of said plant, off-spring, clone or descendant.

The invention further provides a method of influencing the characteristics of a plant comprising expression of a heterologous GAI or gai gene sequence (or mutant, allele, derivative or homologue thereof, as discussed) within cells of the plant. The term "heterologoust" indicates that the gene/sequence of nucleotides in question have been introduced into said cells of the plant, or an ancestor thereof, using genetic engineering, that is to say by human intervention, which may comprise transformation. The gene may be on an extra-genomic vector or incorporated, preferably stably, into the genome. The heterologous gene may replace an endogenous equivalent gene, ie one which normally performs the same or a similar function in control of growth and/or development, or the inserted sequence may be additional to an endogenous gene. An advantage of introduction of a heterologous gene is the ability to place expression of the gene under the control of a promoter of choice, in order to be able to influence gene expression, and therefore growth and/or development of the plant according to preference. Furthermore, mutants and derivatives of the wild-type gene may be used in place of the endogenous gene. The inserted gene may be foreign or exogenous to the host cell, e.g. of another plant species.

The principal characteristic which may be altered using the present invention is growth.

According to the model of the GAI gene as a growth repressor, under-expression of the gene may be used to promote growth, at least in plants which have only one endogenous gene conferring GAI function (not for example *Arabidopsis* which has endogenous homologues which would compensate) . This may involve use of anti-sense or sense regulation. Taller plants may be made by knocking out GAI or the relevant homologous gene in the plant of interest. Plants may be made which are resistant to compounds which inhibit GA biosynthesis, such as paclobutrazol, for instance to allow use of a GA biosynthesis inhibitor to keep weeds dwarf but let crop plants grow tall.

Over-expression of a GAI gene may lead to a dwarf plant which is correctable by treatment with GA, as predicted by the GAI repression model.

Since gai mutant genes are dominant on phenotype, they may be used to make GA-insensitive dwarf plants. This may be applied for example to any transformable crop-plant, tree or fruit-tree species. It may provide higher yield/reduced lodging like Rht wheat. In rice this may provide GA-insensitive rice resistant to the Bakane disease, which is a problem in Japan and elsewhere. Dwarf ornamentals may be of value for the horticulture and cut-flower markets. Sequence manipulation may provide for varying degrees of severity of dwarfing, GA-insensitive phenotype, allowing tailoring of the degree of severity to the needs of each crop-plant or the wishes of the manipulator. Over-expression of gai-mutant sequences is potentially the most useful.

A second characteristic that may be altered is plant development, for instance flowering. In some plants, and in certain environmental conditions, a GA signal is required for floral induction. For example, GA-deficient mutant *Arabidopsis* plants grown under short day conditions will do not flower unless treated with GA: these plants do flower normally when grown under long day conditions. *Arabidopsis* gai mutant plants show delayed flowering under short day conditions: severe mutants may not flower at all. Thus, for instance by GAI or gai gene expression or over-expression, plants may be produced which remain vegetative until given GA treatment to induce flowering. This may be useful in horticultural contexts or for spinach, lettuce and other crops where suppression of bolting is desirable.

The nucleic acid according to the invention may be placed under the control of an externally inducible gene promoter to place the GA or gai coding sequence under the control of the user.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. The preferable situation is where the level of expression increases upon application of the relevant stimulus by an amount effective to alter a phenotypic characteristic. Thus an inducible (or "switchable") promoter may be used which causes a basic level of expression in the absence of the stimulus which level is too low to bring about a desired phenotype (and may in fact be zero). Upon application of the stimulus, expression is increased (or switched on) to a level which brings about the desired phenotype.

Suitable promoters include the Cauliflower Mosaic Virus 35S (CaMV 35S) gene promoter that is expressed at a high level in virtually all plant tissues (Benfey et al, 1990a and 1990b); the maize glutathione-S-transferase isoform II (GST-II-27) gene promoter which is activated in response to application of exogenous safener (WO93/01294, ICI Ltd); the cauliflower meri 5 promoter that is expressed in the vegetative apical meristem as well as several well localised positions in the plant body, eg inner phloem, flower primordia, branching points in root and shoot (Medford, 1992; Medford et al, 1991) and the *Arabidopsis thaliana* LEAFY promoter that is expressed very early in flower development (Weigel et al, 1992).

The GST-II-27 gene promoter has been shown to be induced by certain chemical compounds which can be applied to growing plants. The promoter is functional in both monocotyledons and dicotyledons. It can therefore be used to control gene expression in a variety of genetically modified plants, including field crops such as canola, sunflower, tobacco, sugarbeet, cotton; cereals such as wheat, barley, rice, maize, sorghum; fruit such as tomatoes, mangoes, peaches, apples, pears, strawberries, bananas, and melons; and vegetables such as carrot, lettuce, cabbage and onion. The GST-II-27 promoter is also suitable for use in a variety of tissues, including roots, leaves, stems and reproductive tissues.

Accordingly, the present invention provides in a further aspect a gene construct comprising an inducible promoter operatively linked to a nucleotide sequence provided by the present invention, such as the GAI gene of *Arabidopsis thaliana*, a homologue from another plant species or any mutant, derivative or allele thereof. This enables control of expression of the gene. The invention also provides plants transformed with said gene construct and methods comprising introduction of such a construct into a plant cell and/or induction of expression of a construct within a plant cell, by application of a suitable stimulus, an effective exogenous inducer. The promoter may be the GST-II-27 gene promoter or any other inducible plant promoter.

When introducing a chosen gene construct into a cell, certain considerations must be taken into account, well known to those skilled in the art. The nucleic acid to be inserted should be assembled within a construct which contains effective regulatory elements which will drive transcription. There must be available a method of transporting the construct into the cell. Once the construct is within the cell membrane, integration into the endogenous chromosomal material either will or will not occur. Finally, as far as plants are concerned the target cell type must be such that cells can be regenerated into whole plants.

Selectable genetic markers may be used consisting of chimaeric genes that confer selectable phenotypes such as resistance to antibiotics such as kanamycin, hygromycin, phosphinotricin, chlorsulfuron, methotrexate, gentamycin, spectinomycin, imidazolinones and glyphosate.

An aspect of the present invention is the use of nucleic acid according to the invention in the production of a transgenic plant.

A further aspect provides a method including introducing the nucleic acid into a plant cell and causing or allowing incorporation of the nucleic acid into the genome of the cell.

Any appropriate method of plant transformation may be used to generate plant cells comprising nucleic acid in accordance with the present invention. Following transformation, plants may be regenerated from transformed plant cells and tissue.

Successfully transformed cells and/or plants, i.e. with the construct incorporated into their genome, may be selected following introduction of the nucleic acid into plant cells, optionally followed by regeneration into a plant, e.g. using one or more marker genes such as antibiotic resistance (see above).

Plants transformed with the DNA segment containing the sequence may be produced by standard techniques which are already known for the genetic manipulation of plants. DNA can be transformed into plant cells using any suitable technology, such as a disarmed Ti-plasmid vector carried by Agrobacterium exploiting its natural gene transfer ability (EP-A-270355, EP-A-0116718, NAR 12(22) 8711–87215 1984), particle or microprojectile bombardment (U.S. Pat. No. 5,100,792, EP-A-444882, EP-A-434616) microinjection (WO 92/09696, WO 94/00583, EP 331083, EP 175966, Green et al. (1987) *Plant Tissue and Cell Culture*, Academic Press), electroporation (EP 290395, WO 8706614 Gelvin Debeyser—see attached) other forms of direct DNA uptake (DE 4005152, WO 9012096, U.S. Pat. No. 4,684,611), liposome mediated DNA uptake (e.g. Freeman et al. *Plant Cell Physiol*. 29: 1353 (1984)), or the vortexing method (e.g. Kindle, *PNAS U.S.A.* 87: 1228 (1990d). Physical methods for the transformation of plant cells are reviewed in Oard, 1991, *Biotech. Adv.* 9: 1–11.

Agrobacterium transformation is widely used by those skilled in the art to transform dicotyledonous species. Recently, there has been substantial progress towards the routine production of stable, fertile transgenic plants in almost all economically relevant monocot plants (Toriyama, et al. (1988) *Bio/Technology* 6, 1072–1074; Zhang, et al. (1988) *Plant Cell Rep*. 7, 379–384; Zhang, et al. (1988) *Theor Appl Genet* 76, 835–840; Shimamoto, et al. (1989) *Nature* 338, 274–276; Datta, et al. (1990) *Bio/Technology* 8, 736–740; Christou, et al. (1991) *Bio/Technology* 9, 957–962; Peng, et al. (1991) International Rice Research Institute, Manila, Philippines 563–574; Cao, et al. (1992) *Plant Cell Rep*. 11, 585–591; Li, et al. (1993) *Plant Cell Rep*. 12, 250–255; Rathore, et al. (1993) *Plant Molecular Biology* 21, 871–884; Fromm, et al. (1990) *Bio/Technology* 8, 833–839; Gordon-Kamm, et al. (1990) *Plant Cell* 2, 603–618; D'Halluin, et al. (1992) *Plant Cell* 4, 1495–1505; Walters, et al. (1992) *Plant Molecular Biology* 18, 189–200; Koziel, et al., (1993) *Biotechnology* 11, 194–200; Vasil, I. K. (1994) *Plant Molecular Biology* 25, 925–937; Weeks, et al. (1993) *Plant Physiology* 102, 1077–1084; Somers, et al. (1992) *Bio/Technology* 10, 1589–1594; WO92/14828). In particular, Agrobacterium mediated transformation is now emerging also as an highly efficient transformation method in monocots (Hiei et al. (1994) *The Plant Journal* 6, 271–282).

The generation of fertile transgenic plants has been achieved in the cereals rice, maize, wheat, oat, and barley (reviewed in Shimamoto, K. (1994) *Current Opinion in Biotechnology* 5, 158–162.; Vasil, et al. (1992) *Bio/Technology* 10, 667–674; Vain et al., 1995, *Biotechnology Advances* 13 (4): 653–671; Vasil, 1996, *Nature Biotechnology* 14 page 702).

Microprojectile bombardment, electroporation and direct DNA uptake are preferred where Agrobacterium is inefficient or ineffective. Alternatively, a combination of different techniques may be employed to enhance the efficiency of the transformation process, eg bombardment with Agrobacterium coated microparticles (EP-A-486234) or microprojectile bombardment to induce wounding followed by co-cultivation with Agrobacterium (EP-A-486233).

*Brassica napus* transformation is described in Moloney et al. (1989) *Plant Cell Reports* 8: 238–242.

Following transformation, a plant may be regenerated, e.g. from single cells, callus tissue or leaf discs, as is standard in the art. Almost any plant can be entirely regenerated from cells, tissues and organs of the plant. Available techniques are reviewd in Vasil et al., *Cell Culture and Somatic Cel Genetics of Plants, Vol I, II and III, Laboratory Procedures and Their Applications*, Academic Press, 1984, and Weissbach and Weissbach, *Methods for Plant Molecular Biology*, Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

In the present invention, over-expression may be achieved by introduction of the nucleotide sequence in a sense orientation. Thus, the present invention provides a method of influencing a characteristic of a plant, the method comprising causing or allowing expression of nucleic acid according to the invention from that nucleic acid within cells of the plant.

Under-expression of the gene product polypeptide may be achieved using anti-sense technology or "sense regulation". The use of anti-sense genes or partial gene sequences to down-regulate gene expression is now well-established. DNA is placed under the control of a promoter such that transcription of the "anti-sense" strand of the DNA yields RNA which is complementary to normal mRNA transcribed from the "sense" strand of the target gene. For double-stranded DNA this is achieved by placing a coding sequence or a fragment thereof in a "reverse orientation" under the control of a promoter. The complementary anti-sense RNA sequence is thought then to bind with mRNS to form a duplex, inhibiting translation of the endiogenous mRNA from the target gene into protein. Whether or not this is the actual mode of action is still uncertain. However, it is established fact that the technique works. See, for example, Rothstein et al, 1987; Smith et al, (1988) *Nature* 334, 724–726; Zhang et al, (1992) *The Plant Cell* 4, 1575–1588, English et al., (1996) *The Plant Cell* 8, 179–188. Antisense technology is also reviewed in reviewed in Bourque, (1995), *Plant Science* 105, 125–149, and Flavell, (1994) *PNAS USA* 91, 3490–3496.

The complete sequence corresponding to the coding sequence in reverse orientation need not be used. For example fragments of sufficient length may be used. It is a routine matter for the person skilled in the art to screen fragments of various sizes and from various parts of the coding sequence to optimise the level of anti-sense inhibition. It may be advantageous to include the initiating methionine ATG codon, and perhaps one or more nucleotides upstream of the initiating codon. A further possibility is to target a regulatory sequence of a gene, e.g. a sequence that is characteristic of one or more genes in one or more pathogens against which resistance is desired. A suitable fragment may have at least about 14–23 nucleotides, e.g. about 15, 16 or 17, or more, at least about 25, at least about 30, at least about 40, at least about 50, or more. Such fragments in the sense orientation may be used in co-suppression (see below).

Total complementarity of sequence is not essential, though may be preferred. One or more nucleotides may differ in the anti-sense construct from the target gene. It may be preferred for there to be sufficient homology for the respective anti-sense and sense RNA molecules to hybridise, particularly under the conditions existing in a plant cell.

Thus, the present invention also provides a method of influencing a characteristic of a plant, the method comprising causing or allowing anti-sense transcription from nucleic acid according to the invention within cells of the plant.

When additional copies of the target gene are inserted in sense, that is the same, orientation as the target gene, a range of phenotypes is produced which includes individuals where over-expression occurs and some where under-expression of protein from the target gene occurs. When the inserted gene is only part of the endogenous gene the number of under-expressing individuals in the transgenic population increases. The mechanism by which sense regulation occurs, particularly down-regulation, is not well-understood. However, this technique is also well-reported in scientific and patent literature and is used routinely for gene control. See, for example, See, for example, van der Krol et al., (1990) *The Plant Cell* 2, 291–299; Napoli et al., (1990) *The Plant Cell* 2, 279–289; Zhang et al., (1992) *The Plant Cell* 4, 1575–1588, and U.S. Pat. No. 5,231,020.

Thus, the present invention also provides a method of influencing a characteristic of a plant, the method comprising causing or allowing expression from nucleic acid according to the invention within cells of the plant. This may be used to influence growth.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE DRAWINGS

The following Figures are included herein:

FIG. 2: The gai-t6 line contains a transposed Ds which interrupts a transcribed gene.

FIG. 3: A nucleotide sequence of (SEQ ID NO:1) a GAI gene encoding a polypeptide with GAI function.

FIG. 4: Primary structure of GAI and gai proteins. The amino acid sequence (SEQ ID NO:2) predicted from the genomic DNA sequence of GAI is shown. The 17 amino acid segment deleted in gai is shown in bold face and double-underlined.

FIG. 5: De-repression model for plant growth regulation by GA.

FIG. 6: Nucleotide and encoded amino acid sequences of gai-derivative alleles.

FIG. 6a: Nucleotide sequence of gai-d1 (SEQ ID NO:3).

FIG. 6b: Amino acid sequence of gai-d1 (SEQ ID NO:4).

FIG. 6c: Nucleotide sequence of gai-d2 (SEQ ID NO:5).

FIG. 6d: Amino acid sequence of gai-d2 (SEQ ID NO:6).

FIG. 6e: Nucleotide sequence of gai-d5 (SEQ ID NO:7).

FIG. 6f: Amino acid sequence of gai-d5 (SEQ ID NO:8).

FIG. 6g: Nucleotide sequence of gai-d7 (SEQ ID NO:9).

FIG. 6h: Amino acid sequence of gai-d7 (SEQ ID NO:10).

DESCRIPTION OF THE INVENTION

EXAMPLE 1

Cloning of and Characterisation of GAI and Gai Genes gai maps to chromosome 1[2] of *Arabidopsis*, approximately 11 cM from a T-DNA insertion carrying a Ds transposon[5,15]. Genetic analyses suggested that loss-of-function alleles confer a tall phenotype indistinguishable from that conferred by the wild-type allele (GAI)[5,6]. We attempted to clone GAI via insertional mutagenesis, exploiting the tendency of Ds to transpose preferentially to linked sites[16,17].

Figure 1:
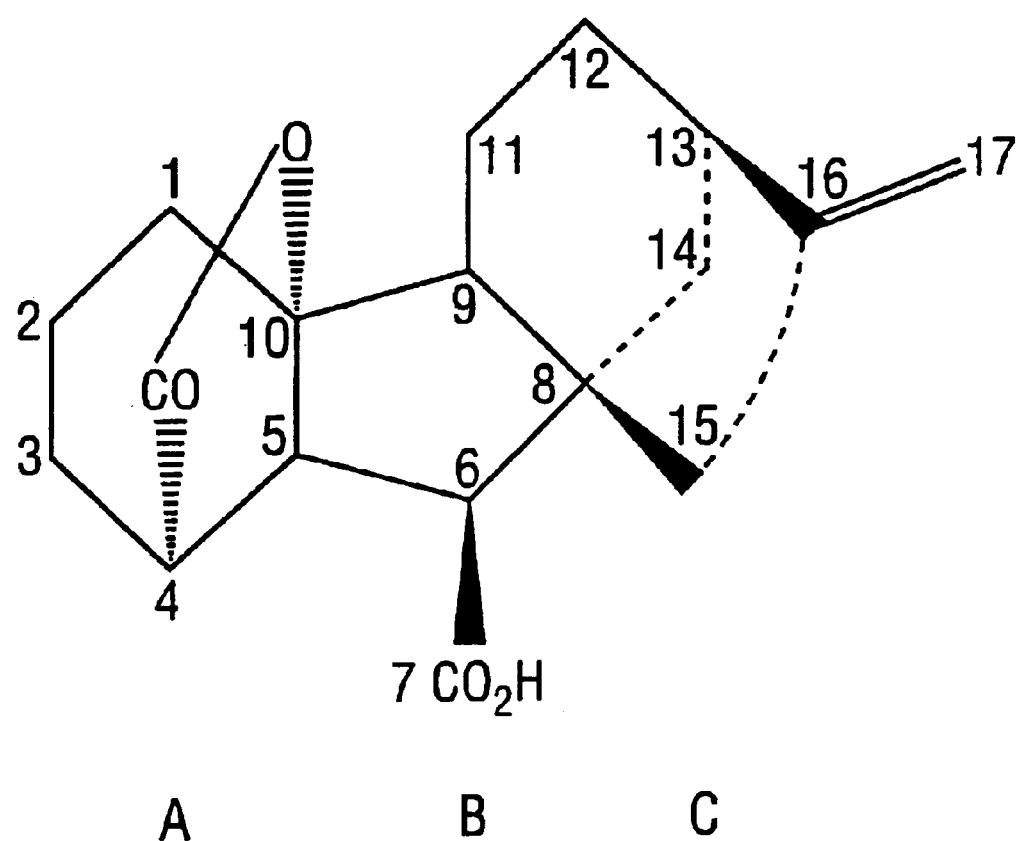
FIG. 1: The basic carbon-ring structure of gibberellins.
Figure 2A:
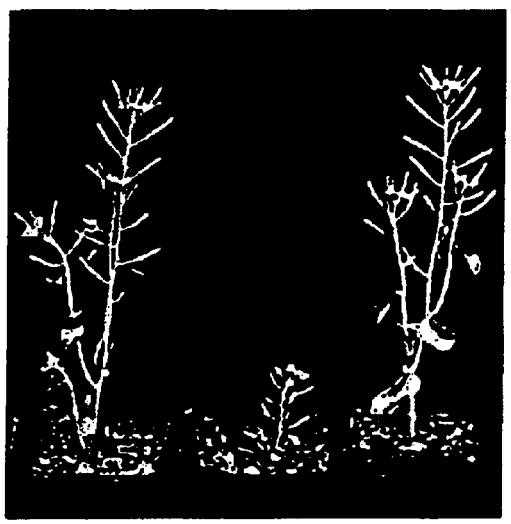
FIG. 2a: Plants shown are (left to right) homozygous for GAI, gai and gai-t6. GAI and gai-t6 plants are indistinguishable.

Plant lines homozygous for A264 and gai, containing a transgene (ΔNaeI-sAc(GUS)-1) expressing Ac transposase were constructed. Plants homozygous for a putative Ds insertion allele, which we designated gai-t6, were isolated from this material as follows[5]. The material was bulked up, by self-pollination, over several generations. During this bulking, searches were made for plants which had stem branches more elongated than expected for a gai homozygote. Seeds obtained from self-pollination of such branches were planted out for closer examination. The progeny of one such branch segregated plants, at a frequency of approximately one quarter, displaying a tall phenotype indistinguishable from that conferred by GAI (FIG. 2a). These plants were homozygous for a new gai allele, which we designated gai-t6.

Figure 2B:
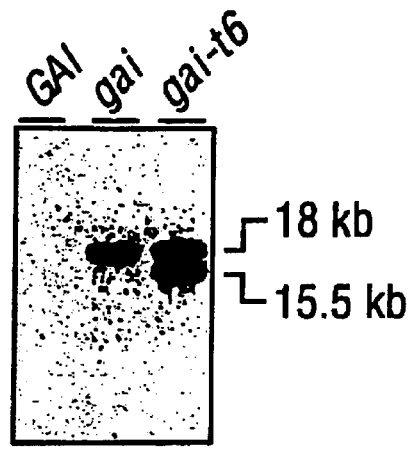
FIG. 2b: DNA gel-blot hybridization using a Ds probe. DNA in the GAI lane lacks Ds. The gai lane contains DNA from plants homozygous for gai and for T-DNA A264[5], which contains Ds (18.0 kb EcoRI fragment). The gai-t6 lane contains DNA from plants homozygous for A264 and for a transposed Ds (15.5 kb fragment).

DNA gel-blot experiments revealed that gai-t6 contains a transposed Ds (FIG. 2b), inserted within a region (approximately 200 kb) of chromosome 1 known to contain GAI (data not shown). Genomic DNA preparation and gel-blot hybridizations were performed as described[5]. EcoRI digests were hybridized with the Ds probe (radiolabelled 3.4 kb XhoI-BamHI subfragment of Ac). gai-t6 has lost (ΔNaeI-sAc(GUS)-1) via genetic segregation.

Figure 2C:
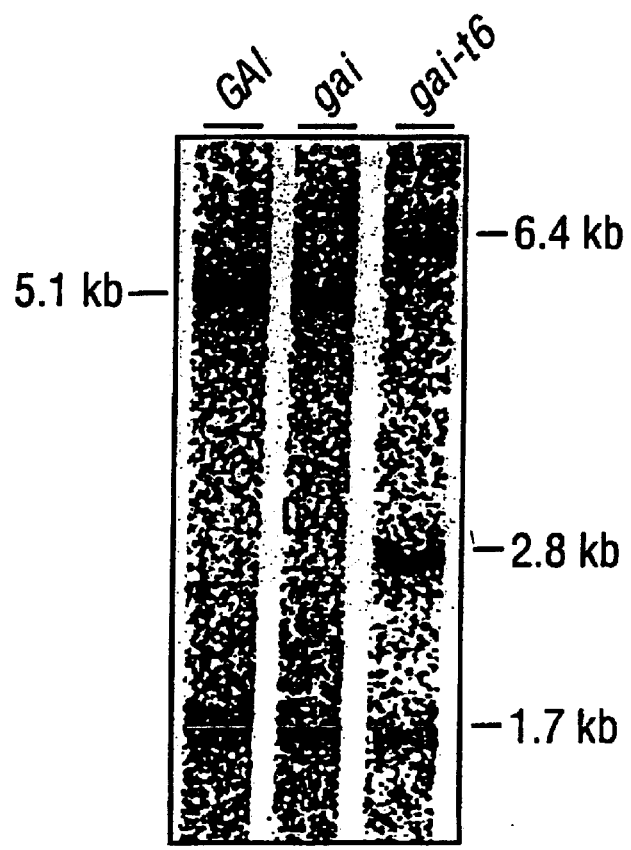
FIG. 2c: DNA gel-blot hybridization using a radiolabelled GAI cDNA probe. The cDNA hybridizes with a 5.1 kb BclI fragment in DNA from GAI and gai, replaced in gai-t6 by fragments of 6.4 and 2.8 kb. Since BclI cuts once within Ds, the Ds insertion is flanked on either side by the gene (GAI) encoding the cDNA. The fainter hybridization at 1.7 kb is one of several seen on longer exposure and identifies a sequence related to GAI.

Further experiments showed that the transposed Ds interrupts the transcribed region of a gene (GAI), and that the Arabidopsis genome contains at least one additional gene sharing significant sequence homology with GAI (FIG. 2c). A radiolabelled IPCR fragment containing genomic DNA adjacent to the 3' end of the transposed Ds in gai-t6 was isolated as previously described[24]. It was necessary to use considerable caution in the use of this probe since it was potentially contaminated with sequence derived from the T-DNA 3' of the Ds in A264 (which is still present in the gai-t6 line): However, the fact that the probe hybridized with DNA from plants lacking any T-DNA insertion indicated that it was useful for the purposes of cloning the region of genomic DNA into which the transposed Ds in gai-t6 had inserted. This probe was shown to hybridize to genomic DNA cosmid clones previously identified as being likely to contain GAI by map-based cloning. One of these cosmids was used to identify, by hybridization, clones from a cDNA library made from mRNA isolated from aerial plant parts (Arabidopsis). These cDNAs were classified according to their hybridization to genomic DNA from GAI, gai and gai-t6. Some of these clones hybridized weakly fragments containing GAI (as defined by the alteration in fragment size caused by the Ds insertion in gai-t6), but more strongly to other, related sequencs. These cDNAs are presumably derived from mRNAs transcribed from genes related in sequence to GAI, but not from GAI itself, and were put to one side for future investigations. One cDNA, pPC1, hybridized strongly to GAI, and less strongly to the fragments containing sequence related to GAI. The DNA sequence of part this cDNA was identical with approximately 150 bp of genomic DNA flanking the Ds insertion in gai-t6.

Reversion analysis showed that excision of Ds from gai-t6 was associated with restoration of a dominant dwarf phenotype.

The DNA sequences of two overlapping GAI cDNAs revealed an open reading frame (ORF) encoding a protein (GAI) of 532 amino acid residues. DNA fragments containing this ORF were amplified from GAI and gai genomic DNA. Oligonucleotide primers derived from the DNA sequences of overlapping cDNAs pPC1 and pPC2 were used to amplify, via PCR, 1.7 kb fragments from GAI and gai genomic DNA. The sequences of the primers used were:

```
Primer N6          5'TAG AAG TGG TAG TGG3';
(SEQ ID NO:11):

Primer AT1         5'ACC ATG AGA CCA GCC G3'.
(SEQ ID NO:12):
```

The sequence of primer AT1 differs by one base from the sequence of the genomic and c-DNA clones. The primer was synthesized very early in the sequencing project, before the final corrected version of the sequence was available.

The DNA sequences of fragments from duplicate amplifications were determined, thus avoiding errors introduced by PCR.

The GAI genomic sequence was almost identical with that of the overlapping cDNAs. There were three nucleotide substitutions that could be due to differences between ecotypes and which do not alter the predicted amino acid sequence of GAI. The sequences of these genomic fragments revealed that the ORF is not interrupted by introns (FIG. 3).

The Ds insertion in gai-t6 is located between the Glu[182] and Asn[183] codons (FIG. 4). The predicted secondary structure of GA: shows few salient features. GAI is a largely hydrophilic protein with a polyhistidine tract of unknown significance close to the amino-terminus, and a weakly hydrophobic domain surrounding a possible glycosylation site at Asn[183]. Computer analysis indicates a relatively low likelihood that this hydrophobic region is a transmembrane domain.

Searches of the DNA and protein sequence databases revealed no domains of obvious functional significance within GAI. gai contains a deletion of 51 bp from within the GAI ORF. This in-frame deletion results in the absence, in gai, of a 17 amino acid residue segment situated close to the amino terminus of the predicted GAI protein (SEQ ID NO:2) (FIG. 4).

Laurenzio et al.[45] reported after the priority date of the present invention a sequence for the SCR (SCARECROW) gene of Arabidopsis, mutation of which results in roots that are missing one cell layer. The disclosed SCR sequence has some homology with the Arabidopsis GAI sequence of the present invention, but lacks the 17 amino acid motif discussed.

A previous publication described the isolation, following γ-irradiation mutagenesis, of gai derivative alleles[5]. These alleles, when homozygous, confer a tall phenotype indistinguishable from that conferred by GAI[5]. Sequencing of amplified fragments from several of the derivative alleles (gai-di, gai-d2, gai-d5 and gai-d7) showed that each contains the 51 bp deletion characteristic of gai. Nucleotide and encoded amino acid sequences of these alleles are shown in FIG. 6 (SEQ ID NO:3 to SEQ ID NO:10). They also contain additional mutations that could confer a non-functional gene product (Table 1). The fact that loss of gai mutant phenotype is correlated with each of these mutations, together with the reversion data (see above), confirms that GAI has been cloned. Furthermore, these results are consistent with predictions that the gai-d alleles would be null alleles[5,6].

Cloning of gai via insertional mutagenesis was possible because it is a gain-of-function mutation. Such mutations can have dominant effects for a variety of reasons, including ectopic or increased expression of a normal gene product, or altered function of a mutant gene product. Here we show that the gai mutation is associated with an altered product. Deletion of a 17 amino acid residue domain from GAI results in a mutant protein (gai) which, in a genetically dominant fashion, causes dwarfism. This strongly suggests that GAI is a growth repressor, and that GA de-represses growth by antagonizing GAI action. The domain missing in the mutant gai protein may be responsible for interacting with the GA signal or with GA itself. gai would then constitutively repress growth because it cannot be antagonized by GA. A de-repression model for GA-mediated plant growth regulation is further elaborated in FIG. 5, but it should be noted that this proposal is not to be taken to limit the scope of the present invention. Knowledge of the actual mode of action of GAI and gai, i.e. how they work, is not a pre-requisite for operation of the present invention, which is founded on cloning of wild-type and mutant versions of the GAI gene.

Mutations at the SPINDLY (SPY) locus of Arabidopsis confer increased resistance to GA biosynthesis inhibitors and a reduced dependence on GA for growth regulation[18], phenotypes characteristic of the slender mutants previously described in other plant species[19-23]. Recent experiments have shown that the dwarf phenotype conferred by gai can be partially suppressed by mutations at SPY and at other loci[6,9]. We propose, again without limiting the scope of the present invention, that SPY, together with proteins encoded by these other loci, is involved with the downstream transduction of the growth repressing signal that originates with GAI (FIG. 5).

According to the model shown in FIG. 5, GA de-represses plant growth because it (or a GA signalling component) antagonizes the activity of GAI, a protein which represses growth. The growth repressing signal is transmitted via spy[6,18], GAR2[6], GAS2 (J.P. and N.P.H., unpublished) and other proteins. Normal plants (GAI) grow tall because the level of endogenous GA is sufficiently high to substantially antagonize the activity of the GAI repressor. GA-deficient plants contain insufficient GA to antagonize GAI repression to the same degree, and are thus dwarfed[25-27]. gai mutant plants are dwarfed[2] because the mutant gai protein is not antagonized by GA, and represses growth in a dominant fashion. spy, gar2 and gas2 mutations partially suppress gai phenotype, and confer resistance to GA biosynthesis inhibitors[6,18]. Pairwise combinations of these three mutations confer more extreme gai suppression and resistance to GA biosynthesis inhibition than is conferred by any of spy, gar2 or gas2 alone. Thus, these genes are proposed to encode downstream components that are responsible for the transmission of the growth repressing signal from GAI. It is possible that the gai mutation is a functional homologue of the GA-insensitivity mutations in maize[10-12] and wheat[13]. Thus this model can be used to provide a general explanation for the regulation of plant growth by GA.

Independent studies of GA-insensitive dwarf mutants in maize[11,12], and GA-independent slender mutants in pea and barley[19-23], have previously implicated the involvement of a repressor function in GA signal-transduction. The indications from the worked desribed herein are that in all probability *Arabidopsis* GAI is such a repressor. An important implication of this is that GA then regulates plant growth not via activation but by de-repression.

EXAMPLE 2

Cloning of GAI Homologues from Wheat, Rice and Brassica sps

DNA containing potential GAI homologues are isolated from wheat, rice and Brassica by reduced stringency probing of cDNA or genomic DNA libraries containing DNA from these species. Hybridizing clones are then purified using standard techniques.

Alternatively, potential GAI homologues are identified by screening of EST databases for cDNA and other sequences showing statistically significant homology with the GAI sequence. Clones are then obtained by requesting them from the relevant distribution centres. Table 2 gives details of results of searching in public sequence databases containing EST sequences that were obtained in random sequencing programmes, showing that homologous sequences have been found in various species, including *Zea Mays* (maize), *O. Sativa* (rice), and *Brassica napus* (rape).

In the case of wheat and maize, it is important to know if these homologous sequences correspond to the previously characterized Rht and D8 genetic loci. This is determined as follows.

cDNA or genomic DNA from rice, wheat or maize is mapped onto the wheat genomic map, thus determining if the map position of the DNA corresponds to the map position of the Rht loci in wheat. Furthermore, in the case of maize, potential transposon-insertion alleles of D8 exist, and these are used to prove the cloning of D8 in the same manner as we have proven the cloning of gai from *Arabidopsis*. By sequencing these various cDNA and genomic DNA clones, studying their expression patterns and examining the effect of altering their expression, genes carrying out a similar function to GAI in regulating plant growth are obtained.

Mutants, derivatives, variants and alleles of these sequences are made and identified as appropriate.

EXAMPLE 3

Expression of GAI and gai Proteins in *E. coli*

DNA fragments containing the complete GAI or gai open reading frames were amplified using PCR from genomic DNA clones (no introns in gene) containing the GAI and gai genes. Amplifications were done using primers which converted the ATG translation start codon into a BamHI restriction endonuclease site. The fragments have a PstI restriction endonuclease site at the other end (beyond the stop codon). The products were cloned and their DNA sequences determined to ensure that no errors had been introduced during the course of the PCR. The correct fragments were cloned into BamHI/PstI digested PQE30 expression vector (Qiaexpressionist kit from the Qiagen Company), resulting in constructs with the potential to express the GAI and gai proteins in *E. coli*. Expression in this vector is regulated by an IPTG-inducible promoter, and the resultant proteins carry an N-terminal polyhistidine tag which can be used to purify them from cellular extracts.

Induction with IPTG resulted in high-level expression of the GAI and gai proteins in *E. coli*.

EXAMPLE 4

Expression Constructs and Transformation of Plants
(a) Normal Expression Levels, Using Endogenous Promoters The GAI and gai genes were isolated as 5 kb EcoRI/EcoRV fragments (containing about 1.5 kb of non-coding sequence flanking the coding sequence) by subcloning from appropriate genomic clones. These fragments were cloned into the Bluescript vector, re-isolated as EcoRI/XbaI fragments, and ligated into binary vectors for mobilisation into *Agrobacterium tumefaciens* C58C1, with the T-DNA being introduced into *Arabidopsis* and tobacco plants as described by Valvekens et al.[32] or by the more recent vacuum infiltration method[33], and into *Brassica napus* using the high efficiency Agrobacterium transformation technique as described in Moloney et al.[34.]
(b) Overexpression Using an Exogenous Promoter Constructs have been made using DNA from vectors pJIT60, containing a double 35S promoter[35] and pJIT62, a modified form of pJIT60 that contains a single 35S promoter. The promoters from these vectors were fused with around 100 bp 5' non-coding sequence, followed by an ATG and the entire GAI or gai open reading frames, followed by a translational stop codon, followed by around 20 bp 3' non-coding sequence, followed by a polyadenylation signal: all this carried on a SstI/XhoI fragment.

This fragment has been ligated into binary vectors for introduction into transgenic plants, either by the use of *Agrobacterium tumefaciens* or as naked DNA, as described earlier.

EXAMPLE 4

Modification of GAI and gai Sequences

A short segment of the GAI open reading frame surrounding the gai deletion is amplified from GAI and gai by using in PCR appropriate oligonucleotide primers, designed on the basis of sequence information provided herein. The amplified segment is then subjected to onr or more of various forms of mutagenesis (see e.g. Sambrook et al.), resulting in a series of overlapping deletion mutants, or, if desired, substitutions of individual nucleotides in this region.

The mutated amplified segment is then substituted for the equivalent segment: in GAI, via restriction endonuclease digestion and a subsequent ligation reaction. This new variant is then expressed in transgenic plants either at normal levels or via overexpression as described above.

Constructs are studied to assess their effects on plant growth regulation in model (e.g. *Arabidopsis* and tobacco) and crop (e.g. wheat, rice and maize) species. Different constructs confer differing degrees of dwarfism and may individually be especially suited to the modification and improvement of particular crop species, or for crops growing in particular environments.

EXAMPLE 5

GAI Null Alleles Confer Increased Resistance to Paclobutrazol

Paclobutrazol is a triazole derivative that specifically inhibits GA biosynthesis at the kaurene oxidase reaction[36, 37], thus reducing endogenous GA levels and conferring a dwarf phenotype on plants exposed to it. The slender mutants of pea and barley are resistant to the dwarfing effects of paclobutrazol[38-42], as is the *Arabidopsis* constitutive GA-response mutant spy[43,44]. Thus, in these mutants stem elongation is at least partially uncoupled from the GA-mediated control characteristic of normal plants. Interestingly, the gai-t6 mutant also displays paclobutrazol resistance. When grown on medium containing paclobutrazol, gai-t6 mutants display longer floral bolt stems than GAI control plants. This result suggests that loss of GAI function causes a reduction in the GA-dependency of stem elongation. Put another way, a GAI null mutant appears to require less endogenous GA to achieve a certain degree of growth than does a normal plant. GA-dependency is not completely abolished by gai-t6 possibly because the products of genes related in sequence to GAI (see above) can substantially, but not completely, compensate for loss of GAI function. These observations are significant, because they demonstrate that the wild-type gene product, GAI, is a GA signal-transduction component.

REFERENCES

1. Hooley, *Plant Mol. Biol.* 26, 1529–1555 (1994).
2. Koornneef et al., *Physiol. Plant.* 65, 33–39 (1985).
3. Talon et al., *Planta* 182, 501–505 (1990).
4. Wilson et al., *Plant Physiol.* 100, 403–408 (1992).
5. Peng et al., *Plant Cell* 5, 351–360 (1993).
6. Wilson et al., *Plant Physiol.* 108, 495–502 (1995) .
7. Putterill et al., *Cell* 80, 847–857 (1995).
8. Xu et al., *Proc. Natl. Acad. Sci. USA* 92, 6640–6644 (1995).
9. Carol et al., *Planta* 197, 414–417 (1995).
10. Fujioka et al., *Proc. Natl. Acad. Sci. USA* 85, 9031–9035 (1988).
11. Harberd et al., *Genetics* 121, 827–838 (1989).
12. Winkler et al., *Planta* 193, 341–348 (1994).
13. Gale et al., *Heredity* 35, 55–65 (1975).
14. Gale et al., Dwarfing genes in wheat. In: Progress in Plant Breeding, G. E. Russell, ed (London: Butterworths) pp 1–35 (1985).
15. Balcells et al., *Trends Biotechnol.* 9, 31–37 (1991).
16. Bancroft et al., *Genetics* 134, 1221–1229 (1993).
17. Jones et al., *Science* 266, 789–793 (1994) .
18. Jacobsen et al., *Plant Cell* 5, 887–896 (1993).
19. Brian et al., *Symp. Soc. Exp. Biol.* 11, 166–182 (1957).
20. Potts et al., *Physiol. Plant.* 63, 357–364 (1985).
21. Lanahan et al., *Planta* 175, 107–114 (1988).
22. Chandler et al., *Planta* 175, 115–120 (1988).
23. Croker et al., *Plant Physiol.* 94, 194–200 (1990).
24. Long et al., *Proc. Natl. Acad. Sci. USA* 90, 10370–10374 (1993).
25. Koornneef et al., *Theor. Appl. Genet.* 58, 257–263 (1980).
26. Talon et al., *Proc. Natl. Acad. Sci. USA* 87, 7983–7987 (1990).
27. Sun et al., *Plant Cell* 6, 1509–1518 (1994).
28. Hoad et al., *Phytochemistry* 20, 703–713 (1981)
29. Serebryakov et al., *Phytochemistry* 23, 1847–1854 (1984).
30. Smith et al., *Phytochemistry* 33, 17–20 (1993).
31. Janknecht et al., *Proc. Natl. Acad. Sci. USA* 88, 8972–8976 (1991).
32. Valvekens et al., *Proc. Natl. Acad. Sci. USA* 85, 5536–5540 (1988).
33. Bechtold et al., *Comptes Rendus de L'Academie des Sciences Serie III—Sciences de la Vie—Life Sciences* 316, 1194–1199 (1993).
34. Moloney et al. (1989) Plant Cell Reports 8: 238–242.
35. Guerineau and Mullineaux, in "Plant Molecular Biology Laboratory Fax", ed RRD Croy, Chapter 4, pp121–147, Blackstone Scientific.
36. Hedden P, Graebe J E (1985) J. Plant Growth Regul 4: 111–122.
37. Davis T D, Curry E A (1991) Crit Rev Plant Sci 10: 151–188.
38. Brian P W (1957) Symp Soc Exp Biol 11: 166–182.
39. Potts W C, Reid J B. Murfet I C (1985) Physiol Plant 63: 357–364.
40. Lanahan M B. Ho T-H D (1988) Planta 175: 107–114.
41. Chandler P M (1988) Planta 175: 115–120.
42. Croker S J, Hedden P, Lenton J R. Stoddart J L (1990) Plant Physiol 94: 194–200.
43. Jacobsen S E, Olszewski N E (1993) Plant Cell 5: 887–896.
44. Jacobsen S E, Binkowski K A, Olszewski N E (1996) Proc Natl Acad Sci, USA 93: 9292–9296.
45. Laurenzio et al. (1996) Cell 86: 423–433.

TABLE 1

Mutations in GAI alleles

| Allele | Nature of Mutation* | Position in Coding Sequence | Consequence of Mutation |
|---|---|---|---|
| gai-d1 | CAG to TAG | Glu$^{239}$ | Stop codon, truncated polypeptide |
| gai-d2 | GAT to GA, one base deletion | Asp$^{274}$ | Frameshift, addition of two novel amino acids, truncated polypeptide |
| gai-d5 | 7 base deletion, also C to G | follows Leu$^{281}$ | Frameshift, addition of 18 novel amino acids, truncated polypeptide |

TABLE 1-continued

Mutations in GAI alleles

| Allele | Nature of Mutation* | Position in Coding Sequence | Consequence of Mutation |
|---|---|---|---|
| gai-d7 | GTT to GT, one base deletion | Val$^{156}$ | Frameshift, addition of 27 novel amino acids, truncated polypeptide |

*Underlining denotes nucleotide substitution in each allele. The alleles were isolated following γ-irradiation mutagenesis of gai homozygotes[5]. 1.7 kb fragments were amplified from genomic DNA from each allele, and sequenced as described above. Each allele contains the 51 bp deletion characteristic of gai, confirming that they are all genuinely derived from gai and are not contaminants.

TABLE 2

Databases searched on Nov. 1, 1996
ESTs with homology to the GAI c-DNA

| Clone ID | Species | Blast Poisson probability |
|---|---|---|
| 1. HOMOLOGY TO THE FIRST 200 AMINOACIDS. | | |
| EM_EST1:ATTS3217 | A. Thaliana | $4.8 \cdot e^{-32}$ |
| EM_EST1:AT7823 | A. Thaliana | $4.8 \cdot e^{-24}$ |
| EM_EST1:AT7938 | A. Thaliana | $7.2 \cdot e^{-22}$ |
| EM_EST3:OSS0803A | O. Sativa (rice) | $7.8 \cdot e^{-11}$ |
| EM_EST1:AT5178 | A. Thaliana | 0.014 |
| EM_EST1:AT9456 | A. Thaliana | 0.026 |
| 2. HOMOLOGY TO AMINOACIDS 200–400. | | |
| EM_EST1:ATTS4818 | A. Thaliana | $1.5 \cdot e^{-21}$ |
| EM_EST3:ZM3101 | Zea Mays (maize) | $9.1 \cdot e^{-14}$ |
| EM_EST1:ATTS1110 | A. Thaliana | $7.9 \cdot e^{-10}$ |
| EM_EST1:ATTS3935 | A. Thaliana | $1.7 \cdot e^{-9}$ |
| EM_STS:ZM7862 | Zea Mays (maize) | $4.5 \cdot e^{-7}$ |
| EM_EST1:AT7938 | A. Thaliana | 0.00011 |
| EM_EST3:OSS3989A | O. Sativa (rice) | 0.00050 |
| 3. HOMOLOGY TO THE LAST 132 AMINOACIDS. | | |
| EM_EST1:AT2057 | A. Thaliana | $3.1 \cdot e^{-52}$ |
| EM_EST1:ATTS3359 | A. Thaliana | $3.2 \cdot e^{-42}$ |
| EM_EST3:OSO713A | O. Sativa (rice) | $2.8 \cdot e^{-10}$ |
| EM_EST1:BN6691 | B. Napus (rape) | $3.0 \cdot e^{-5}$ |
| EM_EST1:ATTS3934 | A. Thaliana | 0.00034 |
| EM_EST1:ATTS4819 | A. Thaliana | 0.00059 |
| EM_EST1:AT4839 | A. Thaliana | 0.00060 |
| EM_EST1:ATTS1327 | A. Thaliana | 0.00073 |
| EM_EST1:AT1868 | A. Thaliana | 0.0054 |
| EM_EST1:AT79316 | A. Thaliana | 0.092 |
| EM_EST1:AT7747 | A. Thaliana | 0.35 |

What is claimed is:

1. An isolated nucleic acid having a nucleotide sequence coding for a polypeptide of which the amino acid sequence comprises the 17 amino acid sequence which is underlined in FIG. 4 (SEQ ID NO: 2) and has at least 95% amino acid sequence identity with the amino acid sequence shown in FIG. 4 (SEQ ID NO. 2), wherein expression of said nucleic acid in a plant results in inhibition of growth of the plant, the inhibition being wholly or partially reversed by gibberellin (GA).

2. An isolated nucleic acid having a nucleotide sequence coding for a polypeptide which comprises the 17 amino acid sequence that is underlined in FIG. 4 (SEQ ID NO:2) and which includes an amino acid sequence which has at least 95% identity with the amino acid sequence shown in FIG. 4 (SEQ ID NO:2), wherein expression of said nucleic acid complements a GAI null mutant phenotype in a plant, such phenotype being resistance to the dwarfing effect of paclobutrazol.

3. The isolated nucleic acid according to claim 1 or 2 wherein said plant is *Arabidopsis thaliana*.

4. The nucleic acid according to claim 1 or 2 further comprising a regulatory sequence for expression.

5. The nucleic acid according to claim 4 wherein the regulatory sequence comprises an inducible promoter.

6. A nucleic acid vector suitable for transformation of a plant cell and comprising the nucleic acid according to claim 1 or 2.

7. A host cell containing the nucleic acid according to claim 1 or 2, wherein said cell is a plant cell or a bacterial cell and wherein said nucleic acid is heterologous to said cell.

8. A plant cell according to claim 7 having said heterologous nucleic acid within its genome.

9. The plant cell according to claim 8 which is comprised in a plant, a plant part or a plant propagule.

10. A method of producing the cell according to claim 7 the method comprising incorporating said nucleic acid into the cell by means of transformation.

11. The method according to claim 10, wherein said nucleic acid is stably incorporated into the genome of said cell.

12. The method according to claim 11 further comprising regenerating a plant from one or more transformed cells.

13. The method according to claim 12 further comprising sexually or asexually propagating or growing off-spring or a descendant of the plant regenerated from said plant cell, wherein said off-sprint or said descendant comprises said nucleic acid.

14. A plant comprising the plant cell according to claim 8.

15. A method of producing a plant, the method comprising incorporating the nucleic acid according to claim 1 or 2 into a plant cell and regenerating a plant from said plant cell.

16. A method of repressing the growth of a plant, the method comprising introducing the nucleic acid according to claim 1 or 2 into cells of the plant and expressing said nucleic acid, wherein expression of said nucleic acid represses plant growth.

17. A method of delaying the flowering time of a plant, the method comprising introducing the nucleic acid according to claim 1 or 2 into cells of the plant and expressing said nucleic acid, wherein expression of said nucleic acid delays flowering time.

* * * * *

SEQUENCE LISTING

<160> NUMBER OF SEQ ID NOS: 12

<210> SEQ ID NO 1
<211> LENGTH: 1964
<212> TYPE: DNA
<213> ORGANISM: Arabidopsis thaliana

<400> SEQUENCE: 1

```
taataatcat ttttttctt ataaccttcc tctctatttt tacaatttat tttgttatta      60
gaagtggtag tggagtgaaa aaacaaatcc taagcagtcc taaccgatcc ccgaagctaa     120
agattcttca ccttcccaaa taaagcaaaa cctagatccg acattgaagg aaaaaccttt     180
tagatccatc tctgaaaaaa aaccaaccat gaagagagat catcatcatc atcatcaaga     240
taagaagact atgatgatga atgaagaaga cgacggtaac ggcatggatg agcttctagc     300
tgttcttggt tacaaggtta ggtcatcgga aatggctgat gttgctcaga aactcgagca     360
gcttgaagtt atgatgtcta atgttcaaga agacgatctt tctcaactcg ctactgagac     420
tgttcactat aatccggcgg agctttacac gtggcttgat tctatgctca ccgaccttaa     480
tcctccgtcg tctaacgccg agtacgatct taaagctatt cccggtgacg cgattctcaa     540
tcagttcgct atcgattcgg cttcttcgtc taaccaaggc ggcggaggag atacgtatac     600
```

```
tacaaacaag cggttgaaat gctcaaacgg cgtcgtggaa accaccacag cgacggctga   660
gtcaactcgg catgttgtcc tggttgactc gcaggagaac ggtgtgcgtc tcgttcacgc   720
gcttttggct tgcgctgaag ctgttcagaa ggagaatctg actgtggcgg aagctctggt   780
gaagcaaatc ggattcttag ctgtttctca atcggagct atgagaaaag tcgctactta    840
cttcgccgaa gctctcgcgc ggcggattta ccgtctctct ccgtcgcaga gtccaatcga   900
ccactctctc tccgatactc ttcagatgca cttctacgag acttgtcctt atctcaagtt   960
cgctcacttc acggcgaatc aagcgattct cgaagctttt caagggaaga aaagagttca  1020
tgtcattgat ttctctatga gtcaaggtct tcaatggccg gcgcttatgc aggctcttgc  1080
gcttcgacct ggtggtcctc ctgttttccg gttaaccgga attggtccac cggcaccgga  1140
taatttcgat tatcttcatg aagttgggtg taagctggct catttagctg aggcgattca  1200
cgttgagttt gagtacagag gatttgtggc taacactttt gctgatcttg atgcttcgat  1260
gcttgagctt agaccaagtg agattgaatc tgttgcggtt aactctgttt tcgagcttca  1320
caagctcttg ggacgacctg gtgcgatcga taaggttctt ggtgtggtga atcagattaa  1380
accggagatt ttcactgtgg ttgagcagga atcgaaccat aatagtccga ttttcttaga  1440
tcggtttact gagtcgttgc attattactc gacgttgttt gactcgttgg aaggtgtacc  1500
gagtggtcaa gacaaggtca tgtcggaggt ttacttgggt aaacagatct gcaacgttgt  1560
ggcttgtgat ggacctgacc gagttgagcg tcatgaaacg ttgagtcagt ggaggaaccg  1620
gttcgggtct gctgggtttg cggctgcaca tattggttcg aatgcgttta agcaagcgag  1680
tatgcttttg gctctgttca acggcggtga gggttatcgg gtggaggaga gtgacggctg  1740
tctcatgttg ggttggcaca cacgaccgct catagccacc tcggcttgga aactctccac  1800
caattagatg gtggctcaat gaattgatct gttgaaccgg ttatgatgat agatttccga  1860
ccgaagccaa actaaatcct actgttttc cctttgtcac ttgttaagat cttatctttc   1920
attatattag gtaattgaaa aatttctaaa ttactcacac tggc                   1964

<210> SEQ ID NO 2
<211> LENGTH: 532
<212> TYPE: PRT
<213> ORGANISM: Arabidopsis thaliana

<400> SEQUENCE: 2

Met Lys Arg Asp His His His His Gln Asp Lys Lys Thr Met Met
  1               5                  10                  15

Met Asn Glu Glu Asp Asp Gly Asn Gly Met Asp Glu Leu Leu Ala Val
                 20                  25                  30

Leu Gly Tyr Lys Val Arg Ser Ser Glu Met Ala Asp Val Ala Gln Lys
             35                  40                  45

Leu Glu Gln Leu Glu Val Met Met Ser Asn Val Gln Glu Asp Asp Leu
         50                  55                  60

Ser Gln Leu Ala Thr Glu Thr Val His Tyr Asn Pro Ala Glu Leu Tyr
 65                  70                  75                  80

Thr Trp Leu Asp Ser Met Leu Thr Asp Leu Asn Pro Ser Ser Asn
                 85                  90                  95

Ala Glu Tyr Asp Leu Lys Ala Ile Pro Gly Asp Ala Ile Leu Asn Gln
            100                 105                 110

Phe Ala Ile Asp Ser Ala Ser Ser Asn Gln Gly Gly Gly Gly Asp
            115                 120                 125

Thr Tyr Thr Thr Asn Lys Arg Leu Lys Cys Ser Asn Gly Val Val Glu
```

-continued

```
        130                 135                 140
Thr Thr Thr Ala Thr Ala Glu Ser Thr Arg His Val Val Leu Val Asp
145                 150                 155                 160

Ser Gln Glu Asn Gly Val Arg Leu Val His Ala Leu Leu Ala Cys Ala
                165                 170                 175

Glu Ala Val Gln Lys Glu Asn Leu Thr Val Ala Glu Ala Leu Val Lys
                180                 185                 190

Gln Ile Gly Phe Leu Ala Val Ser Gln Ile Gly Ala Met Arg Lys Val
                195                 200                 205

Ala Thr Tyr Phe Ala Glu Ala Leu Ala Arg Arg Ile Tyr Arg Leu Ser
    210                 215                 220

Pro Ser Gln Ser Pro Ile Asp His Ser Leu Ser Asp Thr Leu Gln Met
225                 230                 235                 240

His Phe Tyr Glu Thr Cys Pro Tyr Leu Lys Phe Ala His Phe Thr Ala
                245                 250                 255

Asn Gln Ala Ile Leu Glu Ala Phe Gln Gly Lys Lys Arg Val His Val
                260                 265                 270

Ile Asp Phe Ser Met Ser Gln Gly Leu Gln Trp Pro Ala Leu Met Gln
    275                 280                 285

Ala Leu Ala Leu Arg Pro Gly Gly Pro Pro Val Phe Arg Leu Thr Gly
    290                 295                 300

Ile Gly Pro Pro Ala Pro Asp Asn Phe Asp Tyr Leu His Glu Val Gly
305                 310                 315                 320

Cys Lys Leu Ala His Leu Ala Glu Ala Ile His Val Glu Phe Glu Tyr
                325                 330                 335

Arg Gly Phe Val Ala Asn Thr Leu Ala Asp Leu Asp Ala Ser Met Leu
                340                 345                 350

Glu Leu Arg Pro Ser Glu Ile Glu Ser Val Ala Val Asn Ser Val Phe
                355                 360                 365

Glu Leu His Lys Leu Leu Gly Arg Pro Gly Ala Ile Asp Lys Val Leu
                370                 375                 380

Gly Val Val Asn Gln Ile Lys Pro Glu Ile Phe Thr Val Val Glu Gln
385                 390                 395                 400

Glu Ser Asn His Asn Ser Pro Ile Phe Leu Asp Arg Phe Thr Glu Ser
                405                 410                 415

Leu His Tyr Tyr Ser Thr Leu Phe Asp Ser Leu Glu Gly Val Pro Ser
                420                 425                 430

Gly Gln Asp Lys Val Met Ser Glu Val Tyr Leu Gly Lys Gln Ile Cys
                435                 440                 445

Asn Val Val Ala Cys Asp Gly Pro Asp Arg Val Glu Arg His Glu Thr
                450                 455                 460

Leu Ser Gln Trp Arg Asn Arg Phe Gly Ser Ala Gly Phe Ala Ala Ala
465                 470                 475                 480

His Ile Gly Ser Asn Ala Phe Lys Gln Ala Ser Met Leu Leu Ala Leu
                485                 490                 495

Phe Asn Gly Gly Glu Gly Tyr Arg Val Glu Glu Ser Asp Gly Cys Leu
                500                 505                 510

Met Leu Gly Trp His Thr Arg Pro Leu Ile Ala Thr Ser Ala Trp Lys
                515                 520                 525

Leu Ser Thr Asn
                530
```

<210> SEQ ID NO 3

```
<211> LENGTH: 1643
<212> TYPE: DNA
<213> ORGANISM: Arabidopsis thaliana

<400> SEQUENCE: 3
tagaagtggt agtggagtga aaaaacaaat cctaagcagt cctaaccgat ccccgaagct      60
aaagattctt caccttccca aataaagcaa aacctagatc cgacattgaa ggaaaaacct     120
tttagatcca tctctgaaaa aaaaccaacc atgaagagag atcatcatca tcatcatcaa     180
gataagaaga ctatgatgat gaatgaagaa gacgacggta acggcatgga tgttgctcag     240
aaactcgagc agcttgaagt tatgatgtct aatgttcaag aagacgatct ttctcaactc     300
gctactgaga ctgttcacta taatccggcg gagctttaca cgtggcttga ttctatgctc     360
accgacctta atcctccgtc gtctaacgcc gagtacgatc ttaaagctat tcccggtgac     420
gcgattctca atcagttcgc tatcgattcg gcttcttcgt ctaaccaagg cggcggagga     480
gatacgtata ctacaaacaa gcggttgaaa tgctcaaacg cgtcgtgga aaccaccaca      540 gcgacggctg agtcaactcg gcatgttgtc ctggttgact cgcaggagaa cggtgtgcgt     600
ctcgttcacg cgcttttggc ttgcgctgaa gctgttcaga aggagaatct gactgtggcg     660
gaagctctgg tgaagcaaat cggattctta gctgtttctc aaatcggagc tatgagaaaa     720
gtcgctactt acttcgccga agctctcgcg cggcggattt accgtctctc tccgtcgcag     780
agtccaatcg accactctct ctccgatact ctttagatgc acttctacga gacttgtcct     840
tatctcaagt tcgctcactt cacggcgaat caagcgattc tcgaagcttt tcaagggaag     900
aaaagagttc atgtcattga tttctctatg agtcaaggtc ttcaatggcc ggcgcttatg     960
caggctcttg cgcttcgacc tggtggtcct cctgttttcc ggttaaccgg aattggtcca    1020
ccggcaccgg ataatttcga ttatcttcat gaagttgggt gtaagctggc tcatttagct    1080
gaggcgattc acgttgagtt tgagtacaga ggatttgtgg ctaacacttt agctgatctt    1140
gatgcttcga tgcttgagct tagaccaagt gagattgaat ctgttgcggt taactctgtt    1200
ttcgagcttc acaagctctt gggacgacct ggtgcgatcg ataaggttct tggtgtggtg    1260
aatcagatta aaccggagat tttcactgtg gttgagcagg aatcgaacca taatagtccg    1320 atttttcttag atcggtttac tgagtcgttg cattattact cgacgttgtt tgactcgttg    1380
gaaggtgtac cgagtggtca agacaaggtc atgtcggagg tttacttggg taaacagatc    1440
tgcaacgttg tggcttgtga tggacctgac cgagttgagc gtcatgaaac gttgagtcag    1500
tggaggaacc ggttcgggtc tgctgggttt gcggctgcac atattggttc gaatgcgttt    1560
aagcaagcga gtatgctttt ggctctgttc aacggcggtg agggttatcg ggtggaggag    1620
agtgacggct gtctcatgtt ggg                                            1643

<210> SEQ ID NO 4
<211> LENGTH: 221
<212> TYPE: PRT
<213> ORGANISM: Arabidopsis thaliana

<400> SEQUENCE: 4

Met Lys Arg Asp His His His His His Gln Asp Lys Lys Thr Met Met
  1               5                  10                  15

Met Asn Glu Glu Asp Asp Gly Asn Gly Met Asp Val Ala Gln Lys Leu
             20                  25                  30

Glu Gln Leu Glu Val Met Met Ser Asn Val Gln Glu Asp Asp Leu Ser
         35                  40                  45
```

| | | | | | | | | | | | |
|---|---|---|---|---|---|---|---|---|---|---|---|
| Gln | Leu | Ala | Thr | Glu | Thr | Val | His | Tyr | Asn | Pro | Ala | Glu | Leu | Tyr | Thr |
| 50 | | | | | 55 | | | | | 60 | |

Gln Leu Ala Thr Glu Thr Val His Tyr Asn Pro Ala Glu Leu Tyr Thr
 50                  55                  60

Trp Leu Asp Ser Met Leu Thr Asp Leu Asn Pro Pro Ser Ser Asn Ala
 65                  70                  75                  80

Glu Tyr Asp Leu Lys Ala Ile Pro Gly Asp Ala Ile Leu Asn Gln Phe
                 85                  90                  95

Ala Ile Asp Ser Ala Ser Ser Ser Asn Gln Gly Gly Gly Gly Asp Thr
                100                 105                 110

Tyr Thr Thr Asn Lys Arg Leu Lys Cys Ser Asn Gly Val Val Glu Thr
            115                 120                 125

Thr Thr Ala Thr Ala Glu Ser Thr Arg His Val Val Leu Val Asp Ser
130                 135                 140

Gln Glu Asn Gly Val Arg Leu Val His Ala Leu Leu Ala Cys Ala Glu
145                 150                 155                 160

Ala Val Gln Lys Glu Asn Leu Thr Val Ala Glu Ala Leu Val Lys Gln
                165                 170                 175

Ile Gly Phe Leu Ala Val Ser Gln Ile Gly Ala Met Arg Lys Val Ala
                180                 185                 190

Thr Tyr Phe Ala Glu Ala Leu Ala Arg Arg Ile Tyr Arg Leu Ser Pro
            195                 200                 205

Ser Gln Ser Pro Ile Asp His Ser Leu Ser Asp Thr Leu
210                 215                 220

<210> SEQ ID NO 5
<211> LENGTH: 1642
<212> TYPE: DNA
<213> ORGANISM: Arabidopsis thaliana

<400> SEQUENCE: 5

```
tagaagtggt agtggagtga aaaaacaaat cctaagcagt cctaaccgat ccccgaagct     60
aaagattctt caccttccca aataaagcaa aacctagatc cgacattgaa ggaaaaacct    120
tttagatcca tctctgaaaa aaaaccaacc atgaagagag atcatcatca tcatcatcaa    180
gataagaaga ctatgatgat gaatgaagaa acgacggta acggcatgga tgttgctcag    240
aaactcgagc agcttgaagt tatgatgtct aatgttcaag aagacgatct ttctcaactc    300
gctactgaga ctgttcacta taatccggcg gagctttaca cgtggcttga ttctatgctc    360
accgacctta tcctccgtc gtctaacgcc gagtacgatc ttaaagctat tcccggtgac    420
gcgattctca atcagttcgc tatcgattcg gcttcttcgt ctaaccaagg cggcggagga    480
gatacgtata ctacaaacaa gcggttgaaa tgctcaaacg gcgtcgtgga accaccaca    540
gcgacggctg agtcaactcg gcatgttgtc ctggttgact cgcaggagaa cggtgtgcgt    600
ctcgttcacg cgcttttggc ttgcgctgaa gctgttcaga aggagaatct gactgtggcg    660
gaagctctgg tgaagcaaat cggattctta gctgtttctc aaatcggagc tatgagaaaa    720
gtcgctactt acttcgccga agctctcgcg cggcggattt accgtctctc tccgtcgcag    780
agtccaatcg accactctct ctccgatact cttcagatgc acttctacga acttgtcct    840
tatctcaagt tcgctcactt cacggcgaat caagcgattc tcgaagcttt tcaagggaag    900
aaaagagttc atgtcattga ttctctatga gtcaaggtct tcaatggccg gcgcttatgc    960
aggctcttgc gcttcgacct ggtggtcctc ctgttttccg gttaaccgga attggtccac   1020
cggcaccgga taatttcgat tatcttcatg aagtttgggtg taagctggct catttagctg   1080
aggcgattca cgttgagttt gagtacagag gatttgtggc taacacttta gctgatcttg   1140
```

-continued

```
atgcttcgat gcttgagctt agaccaagtg agattgaatc tgttgcggtt aactctgttt      1200
tcgagcttca caagctcttg ggacgacctg gtgcgatcga taaggttctt ggtgtggtga      1260
atcagattaa accggagatt ttcactgtgg ttgagcagga atcgaaccat aatagtccga      1320
ttttcttaga tcggtttact gagtcgttgc attattactc gacgttgttt gactcgttgg      1380
aaggtgtacc gagtggtcaa gacaaggtca tgtcggaggt ttacttgggt aaacagatct      1440
gcaacgttgt ggcttgtgat ggacctgacc gagttgagcg tcatgaaacg ttgagtcagt      1500
ggaggaaccg gttcgggtct gctgggtttg cggctgcaca tattggttcg aatgcgttta      1560
agcaagcgag tatgctttg gctctgttca acggcggtga gggttatcgg gtggaggaga       1620
gtgacggctg tctcatgttg gg                                               1642
```

<210> SEQ ID NO 6
<211> LENGTH: 259
<212> TYPE: PRT
<213> ORGANISM: Arabidopsis thaliana

<400> SEQUENCE: 6

```
Met Lys Arg Asp His His His His Gln Asp Lys Lys Thr Met Met
  1               5                  10                  15

Met Asn Glu Glu Asp Asp Gly Asn Gly Met Asp Val Ala Gln Lys Leu
                 20                  25                  30

Glu Gln Leu Glu Val Met Met Ser Asn Val Gln Glu Asp Asp Leu Ser
             35                  40                  45

Gln Leu Ala Thr Glu Thr Val His Tyr Asn Pro Ala Glu Leu Tyr Thr
         50                  55                  60

Trp Leu Asp Ser Met Leu Thr Asp Leu Asn Pro Ser Ser Asn Ala
 65                  70                  75                  80

Glu Tyr Asp Leu Lys Ala Ile Pro Gly Asp Ala Ile Leu Asn Gln Phe
                 85                  90                  95

Ala Ile Asp Ser Ala Ser Ser Asn Gln Gly Gly Gly Asp Thr
            100                 105                 110

Tyr Thr Thr Asn Lys Arg Leu Lys Cys Ser Asn Gly Val Val Glu Thr
            115                 120                 125

Thr Thr Ala Thr Ala Glu Ser Thr Arg His Val Val Leu Val Asp Ser
        130                 135                 140

Gln Glu Asn Gly Val Arg Leu Val His Ala Leu Leu Ala Cys Ala Glu
145                 150                 155                 160

Ala Val Gln Lys Glu Asn Leu Thr Val Ala Glu Ala Leu Val Lys Gln
                165                 170                 175

Ile Gly Phe Leu Ala Val Ser Gln Ile Gly Ala Met Arg Lys Val Ala
            180                 185                 190

Thr Tyr Phe Ala Glu Ala Leu Ala Arg Arg Ile Tyr Arg Leu Ser Pro
        195                 200                 205

Ser Gln Ser Pro Ile Asp His Ser Leu Ser Asp Thr Leu Gln Met His
    210                 215                 220

Phe Tyr Glu Thr Cys Pro Tyr Leu Lys Phe Ala His Phe Thr Ala Asn
225                 230                 235                 240

Gln Ala Ile Leu Glu Ala Phe Gln Gly Lys Lys Arg Val His Val Ile
                245                 250                 255

Asp Ser Leu
```

<210> SEQ ID NO 7
<211> LENGTH: 1636

<210> SEQ ID NO 7
<211> LENGTH: 1636
<212> TYPE: DNA
<213> ORGANISM: Arabidopsis thaliana

<400> SEQUENCE: 7

| | | | | | |
|---|---|---|---|---|---|
| tagaagtggt | agtggagtga | aaaaacaaat | cctaagcagt | cctaaccgat | ccccgaagct | 60 |
| aaagattctt | caccttccca | aataaagcaa | acctagatc | cgacattgaa | ggaaaaacct | 120 |
| tttagatcca | tctctgaaaa | aaaccaacc | atgaagagag | atcatcatca | tcatcatcaa | 180 |
| gataagaaga | ctatgatgat | gaatgaagaa | gacgacggta | acggcatgga | tgttgctcag | 240 |
| aaactcgagc | agcttgaagt | tatgatgtct | aatgttcaag | aagacgatct | ttctcaactc | 300 |
| gctactgaga | ctgttcacta | taatccggcg | gagctttaca | cgtggcttga | ttctatgctc | 360 |
| accgacctta | tcctccgtc | gtctaacgcc | gagtacgatc | ttaaagctat | tcccggtgac | 420 |
| gcgattctca | atcagttcgc | tatcgattcg | gcttcttcgt | ctaaccaagg | cggcggagga | 480 |
| gatacgtata | ctacaaacaa | gcggttgaaa | tgctcaaacg | gcgtcgtgga | aaccaccaca | 540 |
| gcgacggctg | agtcaactcg | gcatgttgtc | ctggttgact | cgcaggagaa | cggtgtgcgt | 600 |
| ctcgttcacg | cgcttttggc | ttgcgctgaa | gctgttcaga | aggagaatct | gactgtggcg | 660 |
| gaagctctgg | tgaagcaaat | cggattctta | gctgtttctc | aaatcggagc | tatgagaaaa | 720 |
| gtcgctactt | acttcgccga | agctctcgcg | cggcggattt | accgtctctc | tccgtcgcag | 780 |
| agtccaatcg | accactctct | ctccgatact | cttcagatgc | acttctacga | gacttgtcct | 840 |
| tatctcaagt | tcgctcactt | cacggcgaat | caagcgattc | tcgaagcttt | tcaagggaag | 900 |
| aaaagagttc | atgtcattga | tttctctatg | agtcaaggtc | ttgggcgctt | atgcaggctc | 960 |
| ttgcgcttcg | acctggtggt | cctcctgttt | tccggttaac | cggaattggt | ccaccggcac | 1020 |
| cggataattt | cgattatctt | catgaagttg | ggtgtaagct | ggctcattta | gctgaggcga | 1080 |
| ttcacgttga | gtttgagtac | agaggatttg | tggctaacac | tttagctgat | cttgatgctt | 1140 |
| cgatgcttga | gcttagacca | agtgagattg | aatctgttgc | ggttaactct | gttttcgagc | 1200 |
| ttcacaagct | cttgggacga | cctggtgcga | tcgataaggt | tcttggtgtg | gtgaatcaga | 1260 |
| ttaaaccgga | gattttcact | gtggttgagc | aggaatcgaa | ccataatagt | ccgattttct | 1320 |
| tagatcggtt | tactgagtcg | ttgcattatt | actcgacgtt | gtttgactcg | ttggaaggtg | 1380 |
| taccgagtgg | tcaagacaag | gtcatgtcgg | aggtttactt | gggtaaacag | atctgcaacg | 1440 |
| ttgtggcttg | tgatggacct | gaccgagttg | agcgtcatga | aacgttgagt | cagtggagga | 1500 |
| accggttcgg | gtctgctggg | tttgcggctg | cacatattgg | ttcgaatgcg | tttaagcaag | 1560 |
| cgagtatgct | tttggctctg | ttcaacggcg | gtgagggtta | tcgggtggag | gagagtgacg | 1620 |
| gctgtctcat | gttggg | | | | | 1636 |

<210> SEQ ID NO 8
<211> LENGTH: 282
<212> TYPE: PRT
<213> ORGANISM: Arabidopsis thaliana

<400> SEQUENCE: 8

Met Lys Arg Asp His His His His Gln Asp Lys Lys Thr Met Met
 1               5                  10                  15

Met Asn Glu Glu Asp Asp Gly Asn Gly Met Asp Val Ala Gln Lys Leu
                20                  25                  30

Glu Gln Leu Glu Val Met Met Ser Asn Val Gln Glu Asp Asp Leu Ser
         35                  40                  45

Gln Leu Ala Thr Glu Thr Val His Tyr Asn Pro Ala Glu Leu Tyr Thr

|          |          |          |          | 50       |          |          |          |          | 55       |          |          |          |          | 60       |          |          |
|----------|----------|----------|----------|----------|----------|----------|----------|----------|----------|----------|----------|----------|----------|----------|----------|----------|

Trp Leu Asp Ser Met Leu Thr Asp Leu Asn Pro Ser Ser Asn Ala
65                  70                  75                  80

Glu Tyr Asp Leu Lys Ala Ile Pro Gly Asp Ala Ile Leu Asn Gln Phe
                85                  90                  95

Ala Ile Asp Ser Ala Ser Ser Asn Gln Gly Gly Gly Asp Thr
            100                 105                 110

Tyr Thr Thr Asn Lys Arg Leu Lys Cys Ser Asn Gly Val Glu Thr
            115                 120                 125

Thr Thr Ala Thr Ala Glu Ser Thr Arg His Val Val Leu Val Asp Ser
130                 135                 140

Gln Glu Asn Gly Val Arg Leu Val His Ala Leu Leu Ala Cys Ala Glu
145                 150                 155                 160

Ala Val Gln Lys Glu Asn Leu Thr Val Ala Glu Ala Leu Val Lys Gln
                165                 170                 175

Ile Gly Phe Leu Ala Val Ser Gln Ile Gly Ala Met Arg Lys Val Ala
            180                 185                 190

Thr Tyr Phe Ala Glu Ala Leu Ala Arg Arg Ile Tyr Arg Leu Ser Pro
            195                 200                 205

Ser Gln Ser Pro Ile Asp His Ser Leu Ser Asp Thr Leu Gln Met His
210                 215                 220

Phe Tyr Glu Thr Cys Pro Tyr Leu Lys Phe Ala His Phe Thr Ala Asn
225                 230                 235                 240

Gln Ala Ile Leu Glu Ala Phe Gln Gly Lys Lys Arg Val His Val Ile
                245                 250                 255

Asp Phe Ser Met Ser Gln Gly Leu Gly Arg Leu Cys Arg Leu Leu Arg
            260                 265                 270

Phe Asp Leu Val Val Leu Leu Phe Ser Gly
            275                 280

<210> SEQ ID NO 9
<211> LENGTH: 1642
<212> TYPE: DNA
<213> ORGANISM: Arabidopsis thaliana

<400> SEQUENCE: 9
tagaagtggt agtggagtga aaaacaaat cctaagcagt cctaaccgat ccccgaagct      60
aaagattctt caccttccca aataaagcaa aacctagatc cgacattgaa ggaaaaacct    120
tttagatcca tctctgaaaa aaaccaacc atgaagagag atcatcatca tcatcatcaa    180
gataagaaga ctatgatgat gaatgaagaa gacgacggta acggcatgga tgttgctcag    240
aaactcgagc agcttgaagt tatgatgtct aatgttcaag aagacgatct ttctcaactc    300
gctactgaga ctgttcacta taatccggcg gagctttaca cgtggcttga ttctatgctc    360
accgacctta atcctccgtc gtctaacgcc gagtacgatc ttaaagctat tcccggtgac    420
gcgattctca atcagttcgc tatcgattcg gcttcttcgt ctaaccaagg cggcggagga    480
gatacgtata ctacaaacaa gcggttgaaa tgctcaaacg gcgtcgtgga aaccaccaca    540
gcgacggctg agtcaactcg gcatgtgtcc tggttgactc gcaggagaac ggtgtgcgtc    600
tcgttcacgc gcttttggct tgcgctgaag ctgttcagaa ggagaatctg actgtggcgg    660
aagctctggt gaagcaaatc ggattcttag ctgtttctca aatcggagct atgagaaaag    720
tcgctactta cttcgccgaa gctctcgcgc ggcggattta ccgtctctct ccgtcgcaga    780
gtccaatcga ccactctctc tccgatactc ttcagatgca cttctacgag acttgtcctt    840

-continued

```
atctcaagtt cgctcacttc acggcgaatc aagcgattct cgaagctttt caagggaaga      900
aaagagttca tgtcattgat ttctctatga gtcaaggtct tcaatggccg gcgcttatgc      960
aggctcttgc gcttcgacct ggtggtcctc ctgttttccg gttaaccgga attggtccac     1020
cggcaccgga taatttcgat tatcttcatg aagttgggtg taagctggct catttagctg     1080
aggcgattca cgttgagttt gagtacagag gatttgtggc taacacttta gctgatcttg     1140
atgcttcgat gcttgagctt agaccaagtg agattgaatc tgttgcggtt aactctgttt     1200
tcgagcttca caagctcttg ggacgacctg gtgcgatcga taaggttctt ggtgtggtga     1260
atcagattaa accggagatt ttcactgtgg ttgagcagga atcgaaccat aatagtccga     1320
ttttcttaga tcggtttact gagtcgttgc attattactc gacgttgttt gactcgttgg     1380
aaggtgtacc gagtggtcaa gacaaggtca tgtcggaggt ttacttgggt aaacagatct     1440
gcaacgttgt ggcttgtgat ggacctgacc gagttgagcg tcatgaaacg ttgagtcagt     1500
ggaggaaccg gttcgggtct gctgggtttg cggctgcaca tattggttcg aatgcgttta     1560
agcaagcgag tatgcttttg gctctgttca acggcggtga gggttatcgg gtggaggaga     1620
gtgacggctg tctcatgttg gg                                              1642
```

<210> SEQ ID NO 10
<211> LENGTH: 166
<212> TYPE: PRT
<213> ORGANISM: Arabidopsis thaliana

<400> SEQUENCE: 10

```
Met Lys Arg Asp His His His His Gln Asp Lys Lys Thr Met Met
  1               5                  10                  15

Met Asn Glu Glu Asp Asp Gly Asn Gly Met Asp Val Ala Gln Lys Leu
             20                  25                  30

Glu Gln Leu Glu Val Met Met Ser Asn Val Gln Glu Asp Asp Leu Ser
         35                  40                  45

Gln Leu Ala Thr Glu Thr Val His Tyr Asn Pro Ala Glu Leu Tyr Thr
     50                  55                  60

Trp Leu Asp Ser Met Leu Thr Asp Leu Asn Pro Ser Ser Asn Ala
 65                  70                  75                  80

Glu Tyr Asp Leu Lys Ala Ile Pro Gly Asp Ala Ile Leu Asn Gln Phe
                 85                  90                  95

Ala Ile Asp Ser Ala Ser Ser Asn Gln Gly Gly Gly Gly Asp Thr
            100                 105                 110

Tyr Thr Thr Asn Lys Arg Leu Lys Cys Ser Asn Gly Val Val Glu Thr
        115                 120                 125

Thr Thr Ala Thr Ala Glu Ser Thr Arg His Val Ser Trp Leu Thr Arg
    130                 135                 140

Arg Arg Thr Val Cys Val Ser Phe Thr Arg Phe Trp Leu Ala Leu Lys
145                 150                 155                 160

Leu Phe Arg Arg Arg Ile
                165
```

<210> SEQ ID NO 11
<211> LENGTH: 15
<212> TYPE: DNA
<213> ORGANISM: Arabidopsis thaliana

<400> SEQUENCE: 11

```
tagaagtggt agtgg                                                        15
```

```
<210> SEQ ID NO 12
<211> LENGTH: 16
<212> TYPE: DNA
<213> ORGANISM: Arabidopsis thaliana

<400> SEQUENCE: 12
accatgagac cagccg                                               16
```